United States Patent
Lathe et al.

(10) Patent No.: US 6,184,350 B1
(45) Date of Patent: Feb. 6, 2001

(54) HIPPOCAMPUS-ASSOCIATED PROTEINS, DNA SEQUENCES CODING THEREFOR AND USES THEREOF

(75) Inventors: Richard Lathe; Kenneth Andrew Rose, both of Edinburgh (GB); Genevieve Stapleton, Seattle, WA (US)

(73) Assignee: BTG International Limited, London (GB)

(*) Notice: Under 35 U.S.C. 154(b), the term of this patent shall be extended for 0 days.

(21) Appl. No.: 09/270,751

(22) Filed: Mar. 17, 1999

Related U.S. Application Data

(62) Division of application No. 08/845,161, filed on Apr. 21, 1997, now Pat. No. 5,976,850, which is a division of application No. PCT/GB95/02465, filed on Oct. 18, 1995.

(51) Int. Cl.[7] .................................................... C07K 14/00
(52) U.S. Cl. ............................................. 530/350; 530/300
(58) Field of Search ..................................... 530/350, 300

(56) References Cited

FOREIGN PATENT DOCUMENTS 0 648 840 A2    4/1995   (EP) .

OTHER PUBLICATIONS

Noshiro et al. "Molecular cloning and sequence analysis of cDNA encoding . . . " FEBS LETT., vol. 268 No. 1, Jul. 1990, pp. 137–140.

Noshiro et al. "Molecular cloning for cholesterol 7–alpha–hydroxylase . . . " FEBS LETT., vol. 257, No. 1, Oct. 1989, pp. 97–100.

Karam et al. "Polymorphisms of human cholesterol . . . " Biochem. Biophys. Res. Commun., vol. 185 No. 2, 1992, pp. 588–595.

Chung et al. "Structure of a bovine gene for P450c21 . . . " Proc. Natl. Acad. Sci., vol. 83, Jun. 1986, pp. 4243–4247.

Bahmre et al. "Microsomal cytochrome P450 . . . " Biochem. Pharmacology, vol. 44 No. 6, Sep. 25,1992, pp. 1223–1225.

Theron et al. "Evidence that estradiol–2/4–hydroxylase . . . " J. Steroid Biochem., vol. 23 No. 6a, Nov. 1985, pp. 919–927.

Volk. "Mapping of phenytoin–inducible cytochrome p450 . . . " Neuroscience, vol. 42 No. 1, 1991, pp. 215–235.

Anandatheerthavarada et al. "Rat brain cytochromes P–450 . . . " Brain Res., vol. 536 No. 1–2, Dec. 1990, pp. 339–343.

Stryer et al, Biochemistry $2^{nd}$ Ed., W.H. Freeman and Company, San Francisco, p. 629 (1981).

*Primary Examiner*—Karen Cochrane Carlson
(74) *Attorney, Agent, or Firm*—Nixon & Vanderhye

(57) ABSTRACT

This invention provides novel hippocampus-associated proteins and DNA sequences coding therefor. In an investigation of hippocampus-associated proteins by differential screening of a rat hippocampus cDNA library, a cDNA species encoding a novel protein designated Hct-1 was isolated and shown to be a to cytochromes P450. The use of hybridization probes based on the rat Hct-1 sequence has led to the identification of homologues in other mammalian species.

8 Claims, 24 Drawing Sheets

Fig. 1B-1

Figure 1A:
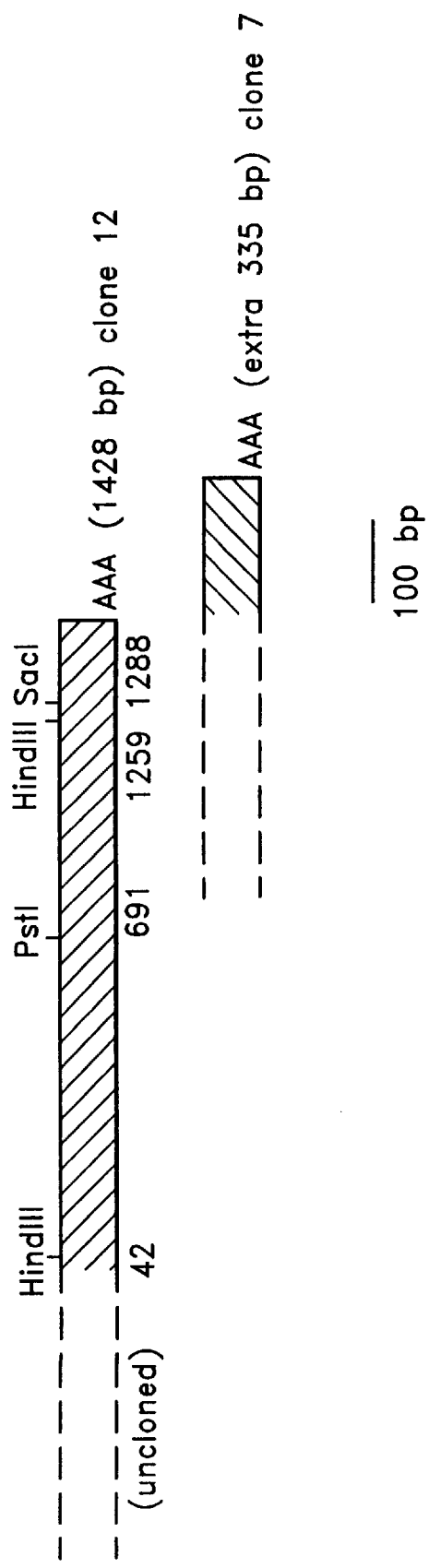

```
  A  L  E  Y  Q  Y  V  M  K  N  P  K  Q  L  S  F  E  K  F  S
GCCTGGAGTACCAGTATGTAATGAAGAACCCAAAACAATTAAGCTTTGAGAAGTTCAGC    60
  R  R  L  S  A  K  A  F  S  V  K  K  L  L  T  N  D  D  L  S
CGAAGATTATCAGGCGAAAGCCTTCTCGTCAAGAAGCTGCTAACTAATGACGACCTTAGC   120
  N  D  I  H  R  G  Y  L  L  L  Q  G  K  S  L  D  G  L  L  E
AATGACATTCACAGAGGCTATCTTCTTTTACAAGGCAAATCTCTGGATGGTCTTCTGGAA   180
  T  M  I  Q  E  V  K  E  I  F  E  S  R  L  L  K  L  T  D  W
ACCATGATCCAAGAAGTAAAAGAAATATTTGAGTCCAGACTGCTAAAACTCACAGATTGG   240
  N  T  A  R  V  F  D  F  C  S  S  L  V  F  E  I  T  F  T  T
AATACAGCAAGAGTATTTGATTTCTGTAGTTCACTGGTATTTGAAATCACATTACAACT    300
  I  Y  G  K  I  L  A  A  N  K  K  Q  I  H  S  E  L  R  D  D
ATATATGGAAAAATTCTGCTAACAAAAACAAATTATCAGTGAGCTGAGGGATGAT       360
  F  L  K  F  D  D  H  F  P  Y  L  V  S  D  I  P  I  Q  L  L
TTTTTAAAATTTGATGACCATTTCCCATACTTAGTATCTGACATACCTATTCAGCTTCTA   420
  R  N  A  E  F  M  Q  K  K  I  I  K  C  L  T  P  E  K  V  A
AGAAATGCAGAATTTATGCAGAAGAAAATTATAAAATGTCTCACCAGAAAAGTAGCT     480
  Q  M  Q  R  R  S  E  I  V  Q  E  R  Q  E  M  L  K  K  Y  Y
CAGATGCAAAGAAGCGGTCAGAAATTGTTCAGGAGAGGCAGGAGATGCTGAAAAATACTAC  560
  G  H  E  E  F  E  I  G  A  H  H  L  G  L  L  W  A  S  L  A
GGGCATGAAGAGTTTGAAATAGGAGCACATCATCTTGGCTTGCTCTGGGCCTCTCTAGCA  600
  N  T  I  P  A  M  F  W  A  M  Y  L  L  Q  H  P  E  A  M
AACACCATTCCAGCTATGTTCTGGGCAATGTATTATCTTCTTCAGCATCCAGAAGCTATG  660
  E  V  L  R  D  E  I  D  S  F  L  Q  S  T  G  Q  K  K  G  P
GAAGTCCTGCGTGACGAAATTGACAGCTTCCTGCAGTCAACAGGTCAAAAGAAAGGACCT  720
```

Fig. 1B-2

```
         G  I  S  V  H  F  T  R  E  Q  L  D  S  L  V  C  L  E  S  A
         GGAATTCTGTCCACTTCACCAGAGAACAATTGGACAGCTTGGTCTGCCTGGAAAGCGCT    780
         I  L  E  V  L  R  L  C  S  Y  S  S  I  I  R  E  V  Q  E  D
         ATTCTGAGGTTCTGAGGTTGTGTCTTACTCCAGCATCATCCGTGAAGTGCAAGAGGAT    840
         M  D  F  S  S  E  S  R  S  Y  R  L  R  K  G  D  F  V  A  V
         ATGGATTTCAGCTCAGAGAGTAGGAGCTACCGTCGCGAAAGGAGACTTTGTAGCTGTC    900
         F  P  P  M  I  H  N  D  P  E  V  F  D  A  P  K  D  F  R  F
         TTTCCTCCAATGATACACAATGACCCAGAAGTCTTCGATGCTCCAAAGGACTTTAGGTTT   960
         D  R  F  V  E  D  G  K  K  K  T  T  F  F  K  G  G  K  K  L
         GATCGCTTCGTAGAAGATGGTAAGAAGAAGACAACGTTTTTCAAGGAGGAAAAAAGCTG  1020
         K  S  Y  I  I  P  F  G  L  G  T  S  K  C  P  G  R  Y  F  A
         AAGAGTTACATTATACCATTTGGACTTGGAACAAGTCTCCAGGCAGATACTTTGCA    1080
         I  N  E  M  K  L  L  V  I  H  L  T  Y  F  F  D  L  E  V  I
         ATTAATGAAATGAAGCTACTAGTGATTATACTTTAACTTATTTTGATTTAGAAGTCATT  1140
         D  T  K  P  I  G  L  N  H  S  R  M  F  L  G  I  Q  H  P  D
         GACACTAAGCCTATAGGACTAAACCACAGTGTTCTGGCATTCAGCATCCAGAC        1200
         S  D  I  S  F  R  Y  K  A  K  S  W  R  S  ***
         TCTGACATCTCATTTAGGTACAAGGCAAAATCTTGGAGATCCTGAAAGGGTGCAGAGAA  1260

GCTTAGCGGAATAAGGCTGCACATGCTGAGCTCTGTGATTTGCTGTACTCCCCAAATGCA  1320

GCCACTATTCTTGTTGTTAGAAATGCAAATTTTTATTTGATTGCGATCCATCCAGTT    1380

TGTTTTGGGTCACAAAACCTGTCATAAAATAAAGCGCTGTCATGGTGTAaaaaaatgtca 1440
```

Fig. 1B-3

```
tggcaatcattcaggataaaataacgtttcaagtttgtactactatgatttt 1500
tatcattgtagtgaatgtgctctttccagtaataaattgcgccaggtgatttttta 1560
attactgaaatccctctaatatcggttttatgtgctgccagaaaagtgtgccatcaatgga 1620
cagtataacaattccagagaaggagaaattaagcccatgagttacgctg 1680
tataaaattgtctcttcaactatatcaataatgtctatatcaccaggttacctttg 1740
cattaaatcgagttttgcaaaag 1763
```

Fig. 3B-2

```
        R   L   S   A   K   A   F   S   V   K   K   L   L   T   D   D   D   L   N   E           134
        GCCGATTATCAGGAAAGCCTTCTCTGTAAAGAAGCTGCTTACTGATGACGACCTTAATG                                480
        D   V   H   R   A   Y   L   L   L   Q   G   K   P   L   D   A   L   L   E   T           154
        AAGACGTTCACAGAGCCTATCTACTTCTACAAGGCAAACCTTTGATGCTCTTCTGAAA                                 540
        M   I   Q   E   V   K   E   L   F   E   S   Q   L   L   K   I   T   D   W   N           174
        CTATGATCCAAGAAGTAAAAGAATTATTTGAGTCCCAACTGCTAAAAATCACAGATTGGA                               600
        T   E   R   I   F   A   F   C   G   S   L   V   F   E   I   T   F   A   T   L           194
        ACACAGAAGAATATTTGCATTCTGTGGCTCACTGTATTTGAGATCACATTTGCGACTC                                 660
        Y   G   K   I   L   A   G   N   K   K   Q   I   I   S   E   L   R   D   D   F           214
        TATATGGAAAATTCTTGCTGGTAACAAGAAACAAATTATCAGTGAGCTAAGGGATGATT                                720
        F   K   F   D   D   M   F   P   Y   L   V   S   D   I   P   I   Q   L   L   R           234
        TTTTAAATTTGATGACATGTTCCCATACTTAGTATCTGACATACCTATTCAGCTTCTAA                                780
        N   E   E   S   M   Q   K   K   I   K   C   L   T   S   E   K   V   A   Q               254
        GAAATGAAGAATCTATGCAGAAGAAAATTATAAATGCCTCACATCAGAAAAGTAGCTC                                 840
        M   Q   G   Q   S   K   I   V   Q   E   S   Q   D   L   L   K   R   Y   Y   R           274
        AGATGCAAGGACAGTCAAAATTGTTCAGGAAAGCCAAGATCTGCTGAAAAGATACTATA                                900
        H   D   D   P   E   I   G   A   H   H   L   G   F   L   W   A   S   L   A   N           294
        GGCATGACGATTCTGAAATAGGAGCACATCATCTTGGCTTTCTCTGGGCCTCTCTAGCAA                               960
        T   I   P   A   M   F   W   A   M   Y   Y   I   L   R   H   P   E   A   M   E           314
        ACACCATTCCAGCTATGTTCTGGGCAATGTATTATATTCTTCGGCATCCTGAAGCTATGG                              1020
        A   L   R   D   E   I   D   S   F   L   Q   S   T   G   Q   K   K   G   P   G           334
        AAGCCCTGCGTGACGAAATTGACAGTTTCCTGCAGTCAACAGGTCAAAAGAAAGGGCCTG                              1080
```

Fig. 3B-3

```
       I   S   V   H   F   T   R   E   Q   L   D   S   L   V   C   L   E   S   T   I      354
GAATTCAGTCCACTTCACCAGAGAACAATTGGACAGCTTGGTCTGCCTGGAAAGCACTA                               1140
       L   E   V   L   R   L   C   S   Y   S   S   I   I   R   E   V   Q   E   D   M      374
TTCTTGAGGTTCTGAGGCTGTGCTCATACTCCAGCATCATCCGAGAAGTGCAGGAGGATA                              1200
       N   L   S   L   E   S   K   S   F   S   L   R   K   G   D   F   V   A   L   F      394
TGAATCTCAGCTTAGAGAGTAAGAGTTTCTCTCTGCGGAAAGGAGATTTGTAGCCCTCT                               1260
       P   P   L   I   H   N   D   P   E   I   F   D   A   P   K   E   F   R   F   D      414
TTCCTCCACTCATACACAATGACCCGGAAATCTTCGATGCTCCAAAGGAATTTAGGTTCG                              1320
       R   F   I   E   D   G   K   K   K   S   T   F   F   K   G   G   K   R   L   K      434
ATCGGTTCATAGAAGATGGTAAGAAGAAAAGCACGTTTTCAAGGAGGGAAGAGGCTGA                                1380
       T   Y   V   M   P   F   G   L   G   T   S   K   C   P   G   R   Y   F   A   V      454
AGACTTACGTTATGCCTTTTGGACTCGGAACAAGTCAGGAGATATTTGCAG                                       1440
       N   E   M   K   L   L   L   I   E   L   L   T   Y   F   D   L   E   I   I   D      474
TGAACGAAATGAAGCTACTGCTTTAACTTATTTGATTGAAATTATCG                                           1500
       R   K   P   I   G   L   N   H   S   R   M   F   L   G   I   Q   H   P   D   S      494
ACAGGAAGCCTATAGGGCTAAATCACAGTGATGTTTTAGTATTCAGCACCCCGATT                                  1560
       A   V   S   F   R   Y   K   A   K   S   W   R   S   *   *   *                      507
CTGCCCGTCTCCTTTAGGTACAAAGCAAATCTTGAGAGCTGAAAGTGTGCAGAGAAG                                 1620
CTTTGCAGAGTAAGGCTGCATGTGCTGAGCTCCGTGATTGGTGCACTCCCCAAATGCA                                1680
ACCGCTACTCTTGTTTGAAAATGGCAAATTTATATTTGGTTGAGATCAATCCAGTTGTT                               1740
```

Fig. 3B-4

```
TTGGGTCACAAACCTGTCATAAATAAAGCAGTGTGATGGTttaaaaatgtcatggca  1800
atcatttcaggataaggtaaaataacatttcaagtttgtactactatgattttatca  1860
tttgtagtgaatgtgctttt  1880
```

Fig. 4A-1

```
MoHct-1    1 MQGATTLDAASPGPLALLGLLFAATLLLSALFLLTRRTRRPREPPLIKGW      50
             |  |||                 |     | ||||  |    ||||  |
HuCYP7     1 M--MTTSLIWGIAIACCCL------WLILGIRRRQTG-EPPLENGL        38

51 GWLPYLGMALKFFKDPLTFLKTLQRQHGDTFTVFLVGKYITFVLNPFQYQVTKNPKQLSFQKF  112
             |||||||  | |   |     |||    ||| |||||||| |  |||  |  | | | ||
          39 GLIPYLGCALQFGANPLEFLRANQRKHGHVFTCKLMGKYFDWKKF                 100

113 SSRLSAKAFSVKKLLT-DDDLNEDVHRAYL-LLQGKPLDALLETMI---QEVKELFESQLLKIT  171
             ||||||||   |          |||   |  || ||| ||| |         |||   |||||
         101 HFATSAKAFGHRSIDPMDGNTTENINDTFIKTLQGHALNSLTESMMENLQRIMRPPVSSNSKTA 164

172 DWNTERIFAFCGSLVFEITFATLYGKILA---GNKKQIISELRDDFFKFDDM-FPYLVSDIPIQ  231
             |||||||||  |||| ||| |||| ||||     ||  |||||| |   ||  | ||| ||||
         165 AWVTEGMYSFCYRVMFEAGYLTIFGRDLTRRDTQKAHILNNL--DNFKQFDKVFPALVAGLPIH  226

240 LLRNEESMQKKIIKCLTSEKVAQMGQSKIVQESQDLLKRYYRHDDPEIGAHHLGFLWASLANT   295
             |     |  | |    |  |   |  |    |  || |||  || |       ||| ||  ||
         227 MFRTAHNAREKLAESLRHENLQKRESISELISLRMFLNDTLSTFDDLEKAKTHLVVLWASQANT  290

296 IPAMFWAMYYILRHPEAMEALRDEIDSFLQSTGQKKG-PGISVHFTREQLDSLVCLESTILEVL  358
             |||| | |||  |  ||||| |    || ||  | |  ||   |    | | ||   | ||
         291 IPATFWSLFQMIRNPEAMKAATEEVKRTLENAGQKVSLEGNPICLSQAELNDLPVLNSIIKESL  354

359 RLCSYSSIIREVQEDMNLSLESKSFSLRKGDFVALFPPLIHNDPEIFDAPKEFRFDRF-IEDGK  421
              || |      |||  |  ||   || | ||   |  | | |||||  |     |    |||
         355 RLSSASLNIRTAKEDFTLHLEDGSYNIRKDSIIALYPQLMHLDPEIYPDPLTFKYDRYLDENGK  418
```

Fig. 4A-2

```
422  KKSTFFKGGKRLKTYVMPFGLGTSKCPGRYFAVNEMKLLLIELLTYFDLEIID--RKPIGLNHS  483
                                    B
     ||   |||  |    ||   ||  ||  | | |  |||  ||   ||     |   |
419  TKTTFYCNGLKLKYYYMPFGSGATICPGRLFAIHEIKQFLILMLSYFELELIEGQAKCPPLDQS  482

484  RMFLGIQHPDSAVSFRYKAKSWRS*  507
     |   |||     |||
483  RAGLGILPPLNDIEFKYKFKHL*  504
```

Fig. 4B

| | | | | | | | | | | | | | | |
|---|---|---|---|---|---|---|---|---|---|---|---|---|---|---|
| MoHct-1 | F | G | L | G | T | S | K | C | P | G | R | Y | F | A |
| HuCYP7  | F | G | S | G | A | T | I | C | P | G | R | L | F | A |
| CYP17   | F | G | A | G | P | R | S | C | V | G | E | M | L | A |
| CYP11B  | F | G | F | G | M | R | Q | C | L | G | R | R | L | A |
| CYP21B  | F | G | C | G | A | R | V | C | L | G | E | P | V | A |
| CYP11A1 | F | G | W | G | V | R | Q | C | L | G | R | R | I | A |
| CYP27   | F | G | Y | G | V | R | A | C | L | G | R | R | I | A |

Fig. 4C

| | | | | | | | | | | | | | | |
|---|---|---|---|---|---|---|---|---|---|---|---|---|---|---|
| MoHct-1 | V | C | L | E | S | T | I | L | E | V | L | R | L | C | S |
| HuCYP7  | P | V | L | N | S | I | K | E | S | L | R | L | S | S |
| CYP17   | V | L | E | H | T | I | R | E | V | L | R | I | R | P |
| CYP11B  | P | L | L | R | A | A | L | K | E | T | L | R | L | Y | P |
| CYP21B  | P | L | L | N | A | T | I | A | E | V | L | R | L | P | V |
| CYP11A1 | P | L | L | K | A | S | I | K | E | T | L | R | L | H | P |
| CYP27   | P | L | L | K | A | V | L | K | E | T | L | R | L | Y | P |

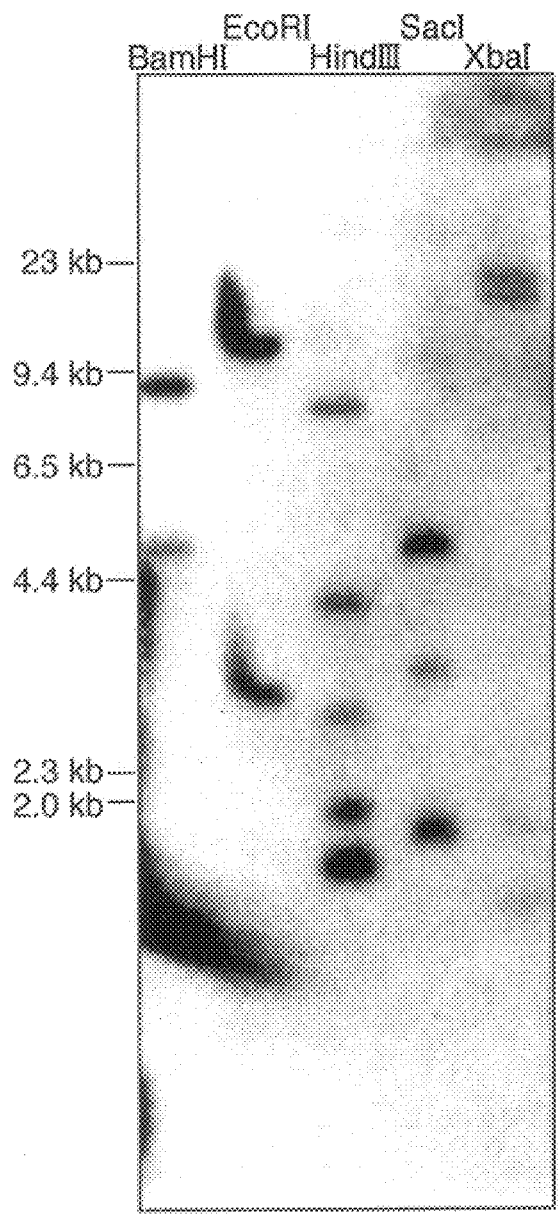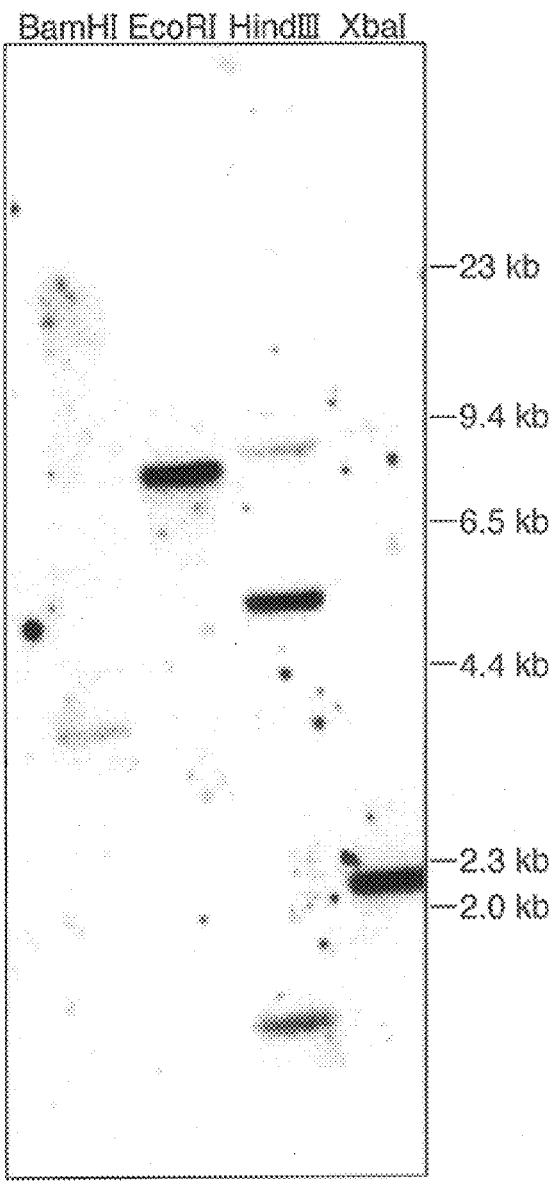

Fig. 9-1

Partial nucleotide sequence of human genomic Hct-1 (CYP7B1) and
the encoded polypeptide

```
ggatccaaccaagtttccagatcttataaatgtggtgaatggtgaatgacttcctgaaga    60 atggatgaatggatgtgttctagtttggaatcctgtgtcagtcacaagtcaatatgtgac   120 cttgaacatgttattaaatctcccacatccataaaagtgaaaatgctggcattagtggat   180 ttttgccagtgttgaattagacatttatttgtgagtacctgctccatacagtatggtcat   240 ttatttgagttaaaattgttgtatttgaacaaaactcagatgacacctaagcatgaaaaa   300
                              intron 2
gctctttatgaagtataaatactcagaaatggaatggcatgttgccaatttgtttctgc    360 tttattgagggaaatatatgagaagtatttaagtcaggggattatgaggaatatttaaag   420 gata(--190nt-)tctagagtgttttccaccatctttcaaaggaaacatgtagtgtacc   680 ttcgaatgaaatggatttgtattaaacttttttgccttagttattagggtctttctaattt   740 ttgattaacatatttttttaatttgtggtgtttatttctgttttattaacaaacgaact   800
                                              GlyLysTyrIleThrPheIleProGlyPro
catatgctcctctctcttttttttttttctGGAAAGTACATAACATTTATACCTGGACCC   860

PheGlnTyrGlnLeuValIleLysAsnHisLysAsnLeuSerPheArgValSerSerAsn
TTCCAGTACCAGCTAGTGATAAAAAATCATAAACAATTAAGCTTTCGAGTATCTTCTAAT   920

LysLeuSerGluLysAlaPheSerIleSerGlnLeuGlnLysAsnHisAspMetAsnAsp
AAATTATCAGAGAAAGCATTTAGCATCAGTCAGTTGCAAAAAAATCATGACATGAATGAT   980

GluLeuHisLeuCysTyrGlnPheLeuGlnGlyLysLysSerLeuAspIleLeuLeuGluSer
GAGCTTCACCTCTGCTATCAATTTTTGCAAGGCAAATCTTTGGACATACTCTTGGAAAGC  1040
                                           exon 3
MetMetGlnAsnLeuLysGlnValPheGluProGlnLeuLeuLysThrThrSerTrpAsp
ATGATGCAGAATCTAAAACAAGTTTTTGAACCCCAGCTGTTAAAAACCACAAGTTGGGAC  1100

ThrAlaGluLeuTyrProPheCysSerSerIleIlePheGluIleThrPheThrThrIle
ACGGCAGAACTGTATCCATTCTGCAGCTCAATAATATTTGAGATCACATTTACAACTATA  1160

TyrGlyLysValIleValCysAspAsnAsnLysPheIleSerGluLeuArgAspAspPhe
TATGGAAAAGTTATTGTTTGTGACAACAACAAATTTATTAGTGAGCTAAGAGATGATTTT  1220

LeuLysPheAspAspLysPheAlaTyrLeuValSerAsnIleProIleGluLeuLeyGly
TTAAAATTTGATGACAAGTTTGCATATTTAGTATCCAACATACCCATTGAGCTTCTAGGA  1280

AsnValLysSerIleArgGluKysIleIleLysCysPheSerSerGluLysLeuAlaLys
AATGTCAAGTCTATTAGAGAGAAAATTATAAAATGCTTCTCATCAGAAAAGTTAGCCAAG  1340

MetGlnGlyTrpSerGluValPheGlnSerArgGlnAspAspLeuGluLysTyrTyrVal
ATGCAAGGATGGTCAGAAGTTTTTCAAAGCAGGCAAGATGACCTGGAGAAATATTATGTG  1400
```

Fig. 9-2

```
HisGluAspLeuGluIleGlyA-
CACGAGGACCTTGAAATAGGAGgtaagaacttctgaatgagcacttgcctaaataaaaat 1460 catttacatagacctctgaaataaaaaaagacaaaatggcgaccttgaaaattttttat 1520 gctctttctaattggctaatgataaatgtttactctgatataacctctataattgatatt 1580 ttttttttgctgaggtggtaaacagatacttaatggtgataatgagaaagcgtataact 1640
                                intron 3
aagctgcatttatccctcttatctcatccccgaccacaccgccccccccatacacattac 1700 attttaaactattctcattaagcagaaaattagacttcagaagcctattggttctcatta 1760 gcatgcagtgatccttggctggtctgtgtcctaacatcttttaattagcacactgcaaat 1820
                                                     -laHisHis
ctaatcagtgtaataaacgctattaatcttcctttacacttattttctcccaCACATCAT 1880

PheGlyPheLeuTrpValSerValAlaSerThrIleProThrMetPheTrpAlaThrTyr
TTAGGCTTTCTCTGGGCCTCTGTGGCAAACACTATTCCAACTATGTTCTGGGCAACGTAT 1940
                                exon 4
TyrLeuLeuArgHisProGluAlaMetAlaAlaValArgAspGluIleAspArgLeuLeu
TATCTTCTGCGGCACCCAGAAGCTATGGCAGCAGTGCGTGACGAAATTGACCGTTTGCTG 2000

GlnSerThrGlyGlnLysGluGlySerGlyPheProIleHisLeuThrArgGluGlnLeu
CAGTCAACAGGTCAAAAGGAAGGGTCTGGATTTCCCATCCACCTCACCAGAGAACAATTG 2060

AspSerLeuIleCysLeu
GACAGCCTAATCTGCCTAGgtaattatttttatctgttatgaagaaagaaggtacctctct 2120 gcaaactcggtttatcactcatagctgtttacaagaggtagaggacacagctgctaattg 2180 acataataactcccatttacatcaattataaattatgtagtttatagccgtagatcatct 2240
                                intron 4
cattgcatgtaaacataaggcctaxgtaattaactgtgxaaxgtatgxaaaaxxctaacc 2300 aaagctt(--550nt-)cctgactgaacttcttactgccaaagttaaattccataccaat 2960 gagttattctctattctctctgtattgacatttcatctgcggtatcctttagggtacaat 3020 attccaagtttctttagacaaacgcaggaacaaatgttcacatatttctgtttctttatt 3080 cctttgacaagtaggcgagcattttagcctatgttggtctcaaaaaaaatcttttaaata 3140 tgttccaggttctttaatgggacctttcaggagcaaaagtcctcccaggtttggtcaatg 3200 ttcaccctcxgtggccattgaggaaaatgcccxxxxxgttctagagattgttctcacttc 3260 tcaggctaaggcccattgagcaatgccagaaagcatgccttatactagcagtcaatttgg 3320 aagttgtagttgtgtctttagcataggttatcaaataaattttatàtttxcttttaaa 3380 aaaatctcaacattactaaaatacaaatatcctttattttctttgcagaattatcggg 3440 gaacaaatccagaaaatttgtgtaaatttcgggtagttgctccacttgatacacagtatt 3500
```

```
tctgcatattgtaatttctatgaagatctaggttgcatttcccatacattcaagcagttt  3560 ccattgcattttatgaataagatgacgcatactgggaagtaaggcaaatacactaaaag  3620 gaatatgtgtttgtattctgtatagttattactcttaaaaaaagtagttgtaattcatcc  3680 actcttttactttcaacttttgctattaaaaaatcattttttaaatttcagtattaaag  3740 cagaaacatttaaatttattagaccagaaaaataacagattctagaactataatttgaat  3800 ccatttaagcccatagctagagctagagattttcactattggatcc  3846
```

Fig. 9-3

Fig. 10

Comparison of human and mouse Hct-1 (Cyp7b1) sequences (exons III and IV)

```
human
G K Y I T F I P G P F Q Y Q L V I K N H K Q L S F R V S S N
| | | | | |   | | | | |   | | | | | | | | | |     | |
G K Y I T F V L N P F Q Y Q Y V T K N P K Q L S F Q K F S S
mouse K L S E K A F S I S Q L Q K N H D M N D E L H L C Y Q F L Q
  |   |   | |     |     | | |       |     |       |     |
R L S A K A F S V K K L L T D D D L N E D V H R A Y L L L Q G K S L D I L L E S M M Q N L K Q V F E P Q L L K T T S W D
| |   | |   | | |   |   | |   |   |     | |   |     |
G K P L D A L L E T M I Q E V K E L F E S Q L L K I T D W N T A E L Y P F C S S I I F E I T F T T I Y G K V I V C D N N
|         | |     | | |   |   |     | |   |
T E R I F A F C G S L V F E I T F A T L Y G K I L A G N K K K F I S E L R D D F L K F D D K F A Y L V S N I P I E L L G
    | | | | | |   | | | |     | | |         |     | |
Q I I S E L R D D F F K F D D M F P Y L V S D I P I Q L L R N V K S I R E K I I K C F S S E K L A K M Q G W S E V F Q S
|     |     | | | | |     |       |   | |         | |
N E E S M Q K K I I K C L T S E K V A Q M Q G Q S K I V Q E ◀─── exon III - exon IV ───▶
R Q D D L E K Y Y V H E D L E I G - A H H F G F L W V S V A
  |   |     |       |       | | | | |       |     |     |
S Q D L L K R Y Y R H D D S E I G - A H H L G F L W A S L A S T I P T M F W A T Y Y L L R H P E A M A A V R D E I D R L
    | | |   | | |   | |     | | | |         | | |   | |
N T I P A M F W A M Y Y I L R H P E A M E A L R D E I D S F L Q S T G Q K E G S G F P I H L T R E Q L D S L I C L
| | | | | |     |         |   | | | | | |     | |
L Q S T G Q K K G P G I S V H F T R E Q L D S L V C L
```

Shared identity = 163/266 residues; 61% identity (74% over exon IV)

Fig. 11A

Kozak sequences in mRNAs for steroidogenic P450's

Nucleotide sequences conforming are in bold; sequences diverging from the consensus are underlined consensus yyRyy ATG R (a)
| | | | |
|---|---|---|---|
| BovCYP21 | - | CTCC<u>A</u>GCC | ATG GTCCTCG |
| HumCYP21 | - | GTCTCGCC | ATG <u>C</u>TGCTCC |
| HumCYP17 | - | CAGCCACC | ATG <u>T</u>GGAGC |
| *Mus*CYP7B | - | TCGTCG<u>GG</u> | ATG <u>C</u>AGGGAG |
| HumCYP7 | - | TTTGCA<u>AA</u> | ATG ATGACCA |
| RatCYP7 | - | TTTGCA<u>AA</u> | ATG ATGACTA |
| MusCYP7 | - | TTTGCA<u>AA</u> | ATG ATGAGCA |
| RabCYP27 | - | TCGGATCC | ATG GCTGCGC |
| RatCYP27 | - | CACGATCT | ATG GCTGTGT |

Sequence selected for the mouse Hct-1 coding sequence in vaccinia virus

*Mus*CYP7B* - TCGCCACC ATG CAGGGAG

Fig. 11B

B. Mutagenesis of the 5' end of the mouse Hct-1 cDNA to create a near-consensus translation initiation region surrounding the ATG (AUG)

(i). Sequence surrounding the initiating ATG and the translation termination site

```
         M  Q  G  A  T  T  L  D  ---           K  S  W  R  S  ...
AGAGCCGCCAGCTCGTCGGGATGCAGGGAGCCACGACCCTAG --- AAATCTTGGAGAAGCTGAAAGTGTGGCAGAGAAG
```

(ii). PCR primers for modification of the translation initiation site and 3' truncation of the cDNA clone

```
         ::::::
         GGCCCTCGAGCCACCATGCAGGGAGCCACG——→
                   |||||||||||||||||||||
AGAGCCGCCAGCTCGTCGGGATGCAGGGAGCCACGACCCTAG --- AAATCTTGGAGAAGCTGAAAGTGTGGCAGAGAAG
                                                |||||||||||||||||||||
                                              ←——AGAACCCTCTTCGACTCTTAAGCCGG
```

5' PRIMER    GGCCCTCGAGCCACCATGCAGGGAGCCACG

3' PRIMER    GGCCGAATTCTCAGCTTCTCCAAGAA

Yeast expression vectors containing the mouse
Hct-1 coding sequence

Clone pMA Not 146 (A) contains the mouse Hct-1 cDNA clone 35; pMA Not 147 (B) contains cDNA clone 40.

HIPPOCAMPUS-ASSOCIATED PROTEINS, DNA SEQUENCES CODING THEREFOR AND USES THEREOF

This is a divisional of application Ser. No. 08/845,161, filed Apr. 21, 1997, now U.S. Pat. No. 5,976,850, which is a divisional of PCT/GB95/02465 filed Oct. 18, 1995.

This invention relates to novel hippocampus-associated proteins, to DNA sequences coding therefor, to uses thereof and to antibodies to said proteins. The novel hippocampus-associated proteins are believed to be of the cytochrome P450 class.

BACKGROUND TO THE INVENTION

The identification of hippocampus-associated proteins and the isolation of cDNA molecules coding therefor is important in the field of neurophysiology. Thus, for example, such proteins are believed to be associated with memory functions and abnormalities in these proteins, including abnormal levels of expression and the formation of modified or mutated protein is considered to be associated with pathological conditions associated with memory impairment. The isolation of novel hippocampus-associated proteins and the associated DNA sequences coding therefor is consequently of considerable importance.

The present invention arose out of our investigation of hippocampus-associated proteins by differential screening of a rat hippocampus cDNA library. A cDNA species encoding a novel protein which we have designated Hct-1 was isolated and shown to be related to cytochromes of the P450 class.

The use of hybridization probes based on the rat Hct-1 sequence has led to the identification of homologues in other mammalian species, specifically mouse and human.

Cytochromes P450 are a diverse group of heme-containing mono-oxygenases (termed CYP's; see Nelson et al., DNA Cell Biol. (1993) 12, 1–51) that catalyse a variety of oxidative conversions, notably of steroids but also of fatty acids and xenobiotics. While CYP's are most abundantly expressed in the testis, ovary, placenta, adrenal and liver, it is becoming clear that the brain is a further site of CYP expression. Several CYP activities or mRNA's have been reported in the nervous system but these are predominantly of types metabolizing fatty acids and xenobiotics (subclasses CYP2C, 2D, 2E and 4). However, primary rat brain-derived glial cells have the capacity to synthesize pregnenolone and progesterone in vitro. Mellon and Deschepper, Brain Res. (1993), 629, 283–292(9) provided molecular evidence for the presence, in brain, of key steroidogenic enzymes CYP11A1 (scc) and CYP11B1 (11 β) but failed to detect CYP17 (c17) or CYP11B2 (AS). Although CYP21A1 (c21) activity is reported to be present in brain, authentic CYP21A1 transcripts were not detected in this tissue.

Interest in steroid metabolism in brain has been fuelled by the finding that adrenal- and brain-derived steroids (neurosteroids) can modulate cognitive function and synaptic plasticity. For instance, pregnenolone and steroids derived from it are reported to have memory enhancing effects in mice. However, the full spectrum of steroid metabolizing CYP's in brain and the biological roles of their metabolites in vivo has not been established.

To investigate such regulation of brain function our studies have focused on the hippocampus, a brain region important in learning and memory. Patients with lesions that include the hippocampus display pronounced deficits in the acquisition of new explicit memories while material encoded long prior to lesion can still be accessed normally. In rat, neurotoxic lesions to the hippocampus lead to a pronounced inability to learn a spatial navigation task, such as the water maze. The role of the hippocampus in learning has been further emphasized by the finding that hippocampal synapses, notably those in region CA1, display a particularly robust form of activity-dependent plasticity known as long term potentiation (LTP). This phenomenon satisfies some of the requirements for a molecular mechanism underlying memory processes—persistence, synapse-specificity and associativity. LTP is thought to be initiated by calcium influx through the NMDA (N-methyl D-aspartate) subclass of receptor activated by the excitatory neurotransmitter, L-glutamate, and occlusion of NMDA receptors in vivo with the competitive antagonist AP5 both blocks LTP and the acquisition of the spatial navigation task.

The induction of LTP is attenuated by simultaneous release of gamma-amino butyric acid (GABA) from inhibitory interneurons: activation of $GABA_A$ receptors antagonizes L-glutamate induced depolarization of the postsynaptic neuron and interplay between the GABA and L-glutamate receptor pathways is thought to modulate the establishment of LTP. Interplay between these two circuits is emphasised by the finding that some aesthetics (e.g. ketamine) act as antagonists of the NMDA receptor while others, such as the steroid aesthetic alfaxolone, are thought to be agonists of the $GABA_A$ receptor. It is of particular note that some naturally occurring steroids, such as pregnenolone sulfate, act as agonists of the $GABA_A$ receptor, while pregnenolone sulfate is also reported to increase NMDA currents. Although neurosteroids principally appear to exert their effects via the $GABA_A$ and NMDA receptors, there have been indications that neurosteroids may also interact with sigma and progesterone receptors.

Despite considerable interest in the action of neuro-active steroids, and possible roles in modulating synaptic plasticity and brain function, little is known of pathways of steroid metabolism in the central nervous system. As part of a study into the molecular biology of the hippocampal formation, and the mechanisms underlying synaptic plasticity, we have sought molecular clones corresponding to mRNA's expressed selectively in the formation. One such cDNA, Hct-1 (forhippocampal transcript), was isolated from a cDNA library prepared from adult rat hippocampus. Sequence analysis has revealed that Hct-1 is a novel cytochrome P450 most closely related to cholesterol- and steroid-metabolizing CYP's but, unlike other CYP's, is predominantly expressed in brain. The present invention provides molecular characterization of Hct-1 coding sequences from rat, mouse and humans, their expression patterns, and discusses the possible role of Hct-1 in steroid metabolism in the central nervous system.

DNA sequences encoding hitherto unknown cytochrome P450 proteins have now been identified and form one aspect of the present invention.

SUMMARY OF THE INVENTION

According to one aspect of the present invention there are thus provided DNA molecules selected from the following:
(a) DNA molecules containing the coding sequence set forth in SEQ Id No: 1 beginning at nucleotide 22 and ending at nucleotide 1541,
(b) DNA molecules containing the coding sequence set forth in SEQ Id No: 2 beginning at nucleotide 1 and ending at nucleotide 1242,
(c) DNA molecules capable of hybridizing with the DNA molecule defined in (a) or (b) under standard hybridization conditions defined as 2×SSC at 65° C.

(d) cytochrome P450-encoding DNA molecules capable of hybridizing with the DNA molecule defined in (a), (b) or (c) under reduced stringency hybridization conditions defined as 6×SSC at 55° C.

Such DNA sequences can represent coding sequences of Hct-1 proteins. The sequences (a) and (b) above represent the mouse and rat Hct-1 gene sequence. Homologous sequences from other vertebrate species, especially mammalian species (including man) fall within the class of DNA molecules represented by (c) or (d).

Thus the present invention further provides a DNA molecule consisting of sequences of the human Hct-1 gene.

These DNA sequences may be selected from the following:

(e) DNA molecules comprising one or more sequences selected from
  (i) the sequence designated "intron 2" in SEQ Id No 3,
  (ii) the sequence designated "exon 3" in SEQ Id No 3,
  (iii) the sequence designated "intron 3" in SEQ Id No 3,
  (iv) the sequence designated "exon 4" in SEQ Id No 3, and
  (v) the sequence designated "intron 5" in SEQ Id No 3; and (f) DNA molecules capable of hybridizing with the DNA molecules defined in (e) under standard hybridization conditions defined as 2×SSC at 65° C.

(g) cytochrome P450-encoding DNA molecules capable of hybridizing with the DNA molecule defined in (e) or (f) under reduced stringency hybridization conditions defined as 6×SSC at 55° C.

(h) DNA molecules comprising contiguous pairs of sequences selected from
  (i) the sequence designated "intron 2" in SEQ Id No 3,
  (ii) the sequence designated "exon 3" in SEQ Id No 3,
  (iii) the sequence designated "intron 3" in SEQ Id No 3,
  (iv) the sequence designated "exon 4" in SEQ Id No 3, and
  (v) the sequence designated "intron 5" in SEQ Id No 3; and (i) DNA molecules capable of hybridizing with the DNA molecules defined in (h) under standard hybridization conditions defined as 2×SSC at 65° C.

(j) cytochrome P450-encoding DNA molecules capable of hybridizing with the DNA molecule defined in (h) or (i) under reduced stringency hybridization conditions defined as 6×SSC at 55° C.

(k) DNA molecules comprising a contiguous coding sequence consisting of the sequences "exon 3" and "exon 4" in SEQ Id No 3, and (l) DNA molecules capable of hybridizing with the DNA molecules defined in (k) under standard hybridization conditions defined as 2×SSC at 65° C.

(m) cytochrome P450-encoding DNA molecules capable of hybridizing with the DNA molecule defined in (k) or (I) under reduced stringency hybridization conditions defined as 6×SSC at 55° C.

It will be appreciated that the DNA sequences that include introns (such as the sequences covered by definitions (e) to (j) above), may consist of or be derived from genomic DNA. Those sequences that exclude introns may also be genomic in origin, but typically would consist of or be or be derived from cDNA. Such sequences could be obtained by probing an appropriate library (cDNA or genomic) using hybridisation probes based upon the sequences provided according to the invention, or they could be prepared by chemical synthesis or by ligation of subsequences.

The invention further provides DNA molecules encoding an Hct-1 gene-associated sequence coded for by a DNA molecule as defined above, but which differ in sequence from said sequences by virtue of one or more amino acids of said Hct-1 gene-associated sequences being encoded by degenerate codons.

The present invention further provide DNA molecules useful as hybridization probes and consisting of a contiguous sequence of at least 18 nucleotides from the DNA sequence set forth in SEQ Id Nos: 1, 2 and 3.

Such molecules preferably contain at least 24 and more preferably at least 30 nucleotide taken from said sequences.

The aforementioned DNA molecules are useful as hybridization probes for isolating members of gene families and homologous DNA sequences from different species. Thus, for example, a DNA sequence isolated from one rodent species, for example rat, has been used for isolating homologous sequences from another rodent species, for example mouse and from other mammalian species, e.g. primate species such as humans.

Such sequences may be further used for isolating homologous sequences from other mammalian species, for example domestic animals such as cows, horses, sheep and pigs, primates such as chimpanzees, baboons and gibbons.

DNA sequences according to the invention may be used in diagnosis of neuropsychiatric disorders, endocrine disorders, immunological disorders, diseases of cognitive function, neurodegenerative diseases or diseases of cognitive function, for example by assessing the presence of depleted levels of mRNA and/or the presence of mutant or modified DNA molecules. Such sequences include hybridisation probes and PCR primers. The latter generally would be short (e.g. 10 to 25) oligonucleotides in length and would be, capable of hybridising with a DNA molecule as defined above. The invention includes the use of such primers in the detection of genomic or cDNA from a biological sample for the purpose of diagnosis of neuropsychiatric disorders, endocrine disorders, immunological disorders, diseases of cognitive function or neurodegenerative diseases.

The present invention further provides hippocampus-associated proteins as such, encoded by the DNA molecules of the invention.

In particular, there is provided
  (i) the protein designated rat Hct-1 comprising the amino acid sequence set forth in SEQ Id No: 1 or a protein having substantial homology thereto,
  (ii) the protein designated mouse Hct-1 comprising the amino acid sequence set forth in SEQ Id No: 2 or a protein having substantial homology thereto, or
  (iii) the protein designated human Hct-1 comprising the amino acid sequence set forth in SEQ Id No: 3 or a protein having substantial homology thereto.

By "substantial homology" is meant a degree of homology such that at least 50%, preferably at least 60% and most preferably at least 70% of the amino acids match. The invention of course covers related proteins having a higher degree of homology, e.g. at least 80%, at least 90% or more.

The Hct-1 polypeptides may be produced in accordance with the invention by culturing a transformed host and recovering the desired Hct-1 polypeptide, characterised in that the host is transformed with nucleic acid comprising a coding sequence as defined above.

Examples of suitable hosts include yeast, bacterial, insect or mammalian cells. Although vectorless expression may be employed, it is preferred that the nucleic acid used to effect the transformation comprises an expression construct or an expression vector, e.g. a vaccinia virus, a baculovirus vector, a yeast plasmid or integration vector.

The invention further provides antibodies, especially monoclonal antibodies which bind to Hct-1 proteins. These and the proteins of the invention may be employed in the design and/or manufacture of an antagonist to Hct-1 protein for diagnosis and/or treatment of diseases of cognitive function or neurodegenerate diseases. The use of Hct-1-associated promoters in the formation of constructs for use in the creation of transgenic animals is also envisaged according to the invention. The antibodies of the invention may be prepared in conventional manner, i.e. by immunising animal such as rodents or rabbits with purified protein obtained from recombinant yeast, or by immunising with recombinant vaccinia.

Hct-1 proteins provided according to the invention posseses catalytic activity, thus they may be used in industrial processes, to effect a catalytic transformation of a substrate. For example, where the substrate is a steroid, the proteins may be used to catalyse stereospecific transformations, e.g. transformations involving oxygen transfer.

DESCRIPTION OF DRAWINGS (see also Figure legends—7 infra

Figure 2A:
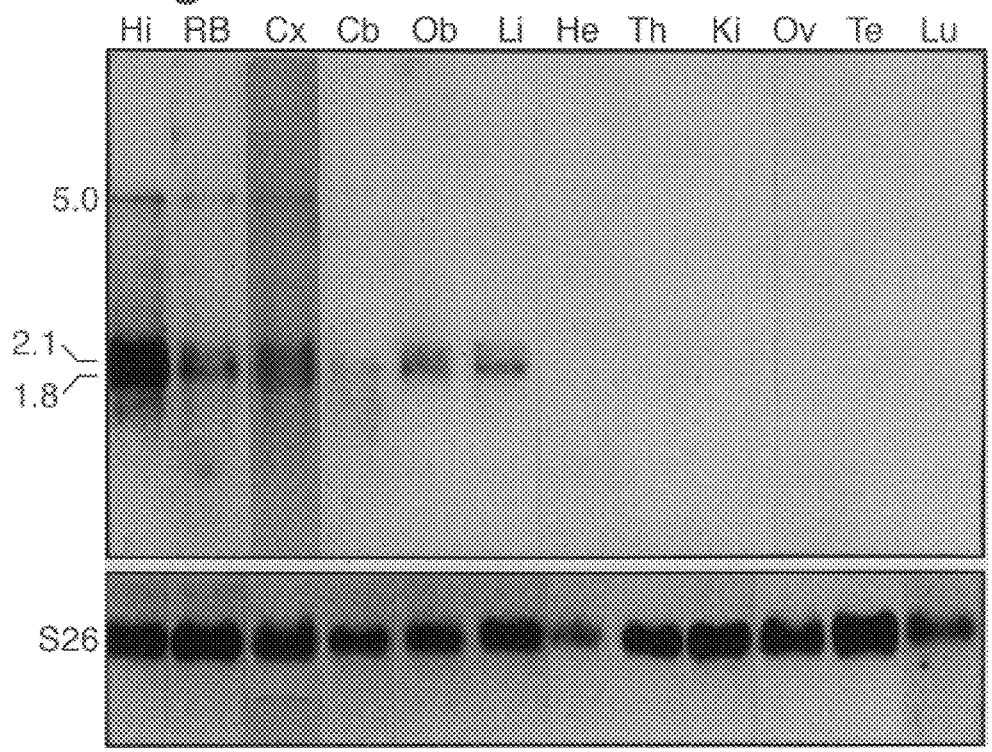
Figure 2B:
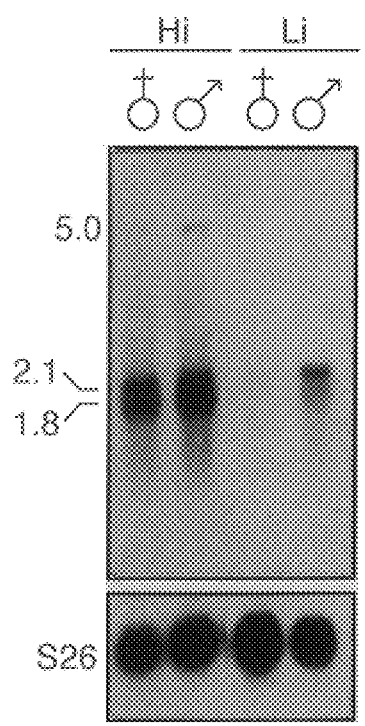
Figure 2C:
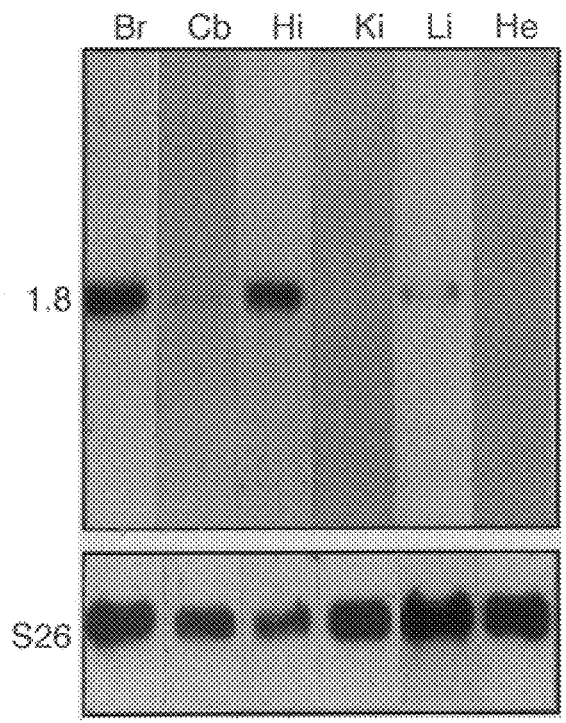
Figures 1, 3A, 3B:
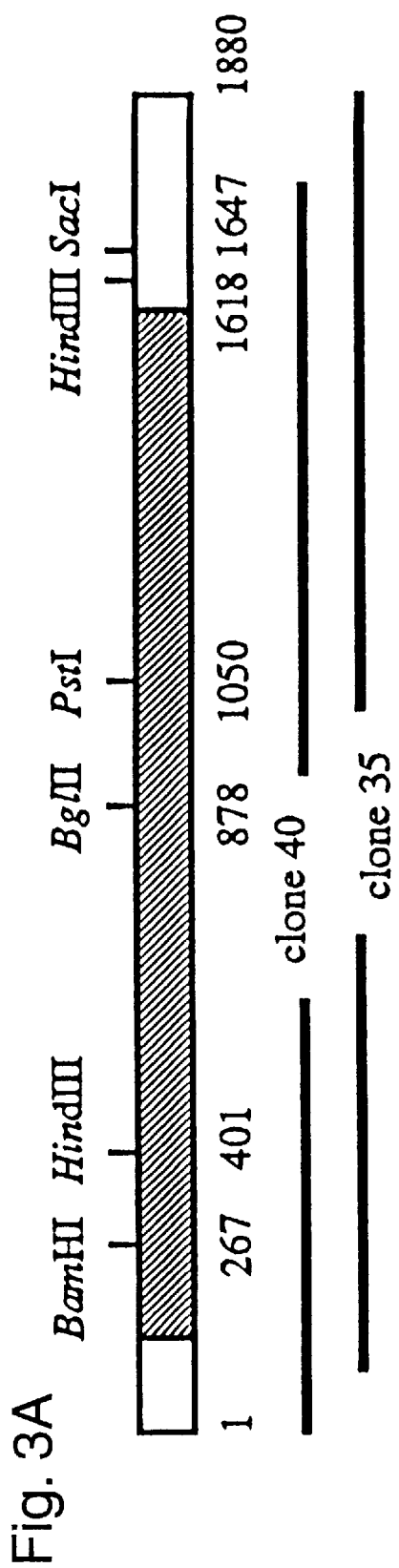
Figure 5A:
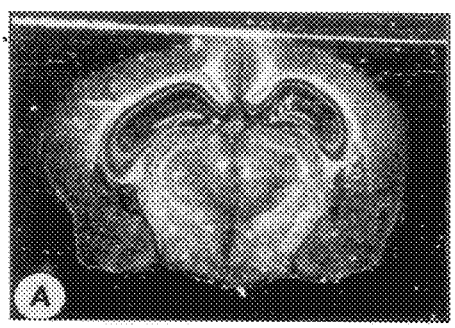
Figure 5B:
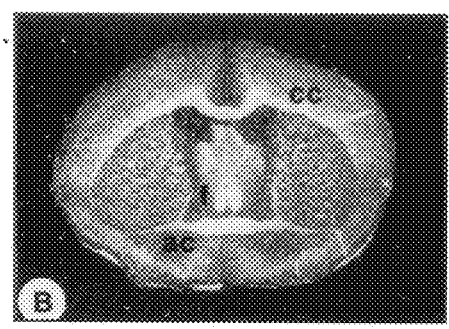
Figure 5C:
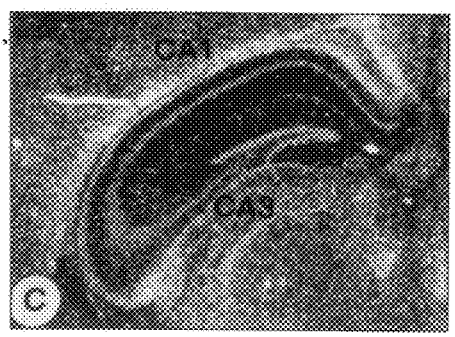
Figure 5D:
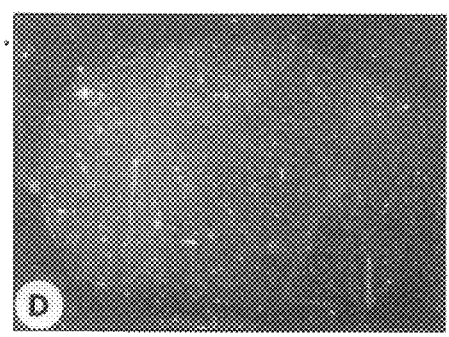
Figure 6:
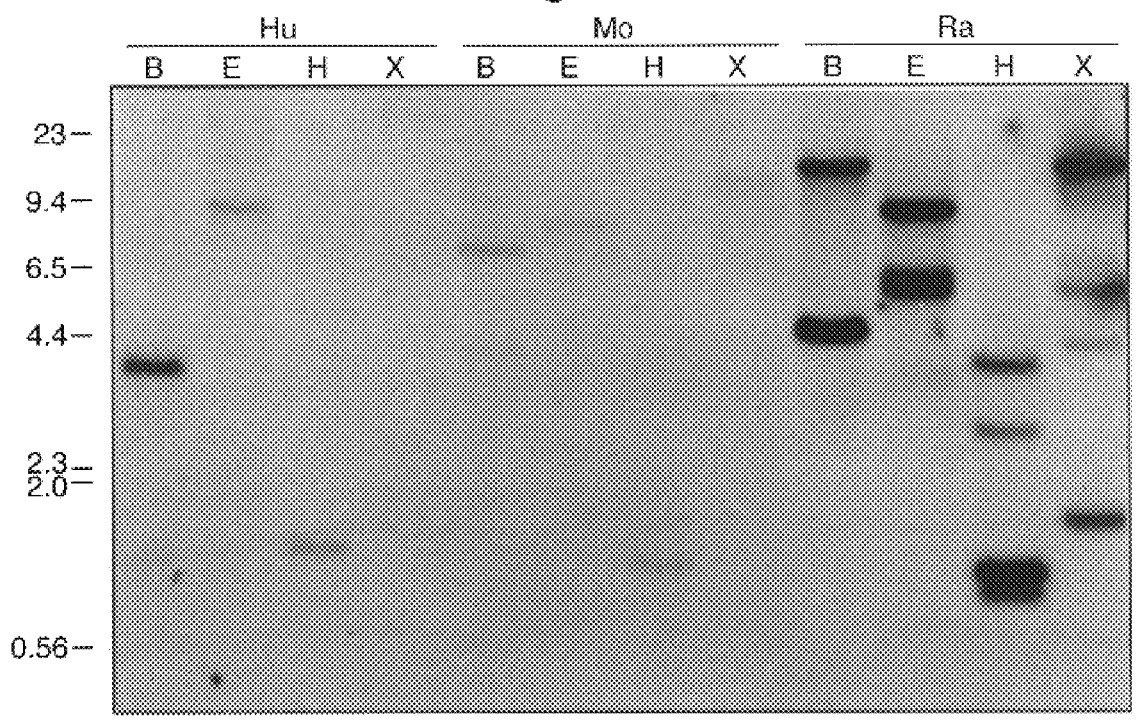

FIG. 1 illustrates (a) a restriction map of clone 12 and (b) the complete nucleotide and translation sequence of the 1.4 kb cDNA clone of rat Hct-1, FIG. 2 illustrates Northern analysis of Hct-1 expression in adult rat and mouse brain, and other tissues, FIG. 3 illustrates (a) restriction maps of clones 35 and 40 and (b) the complete nucleotide and translation sequence of mouse Hct-1 cDNA, FIG. 4 illustrates an alignment of mouse Hct-1 with human CYP7 and highlights regions homologous to other steroidogenic P450s, FIG. 5 illustrates an analysis of Hct-1 expression in mouse brain, FIG. 6 illustrates Southern analysis of Hct-1 coding sequences in mouse, rat and human.

Figure 8:
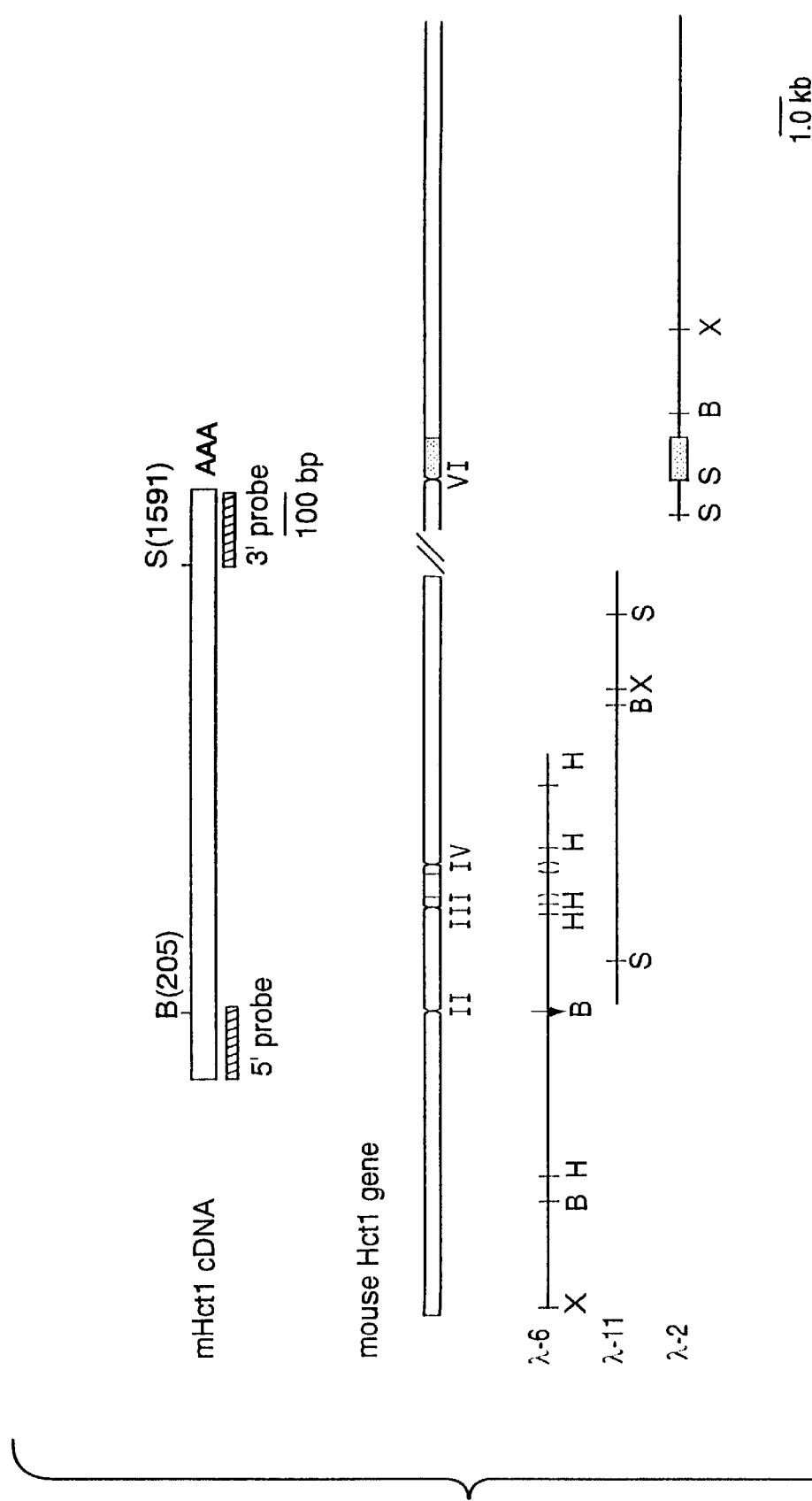
Figure 12A:
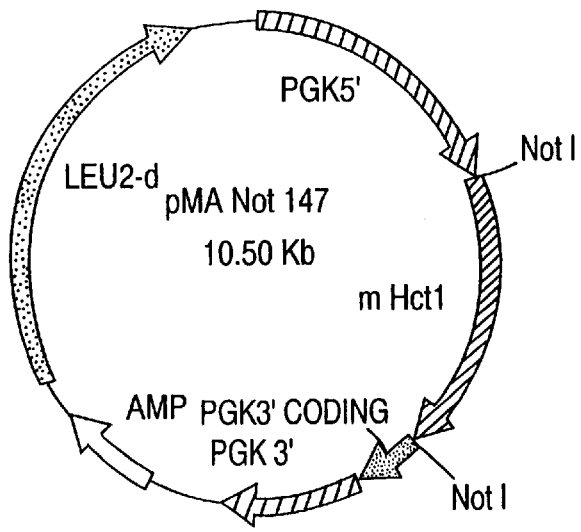
Figure 12B:
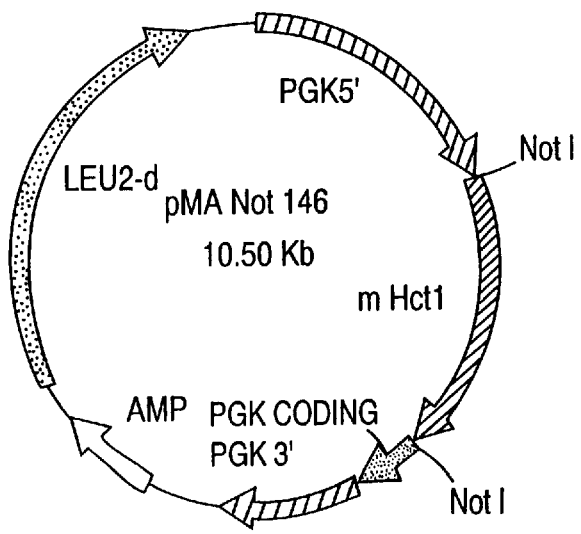
Figure 13:
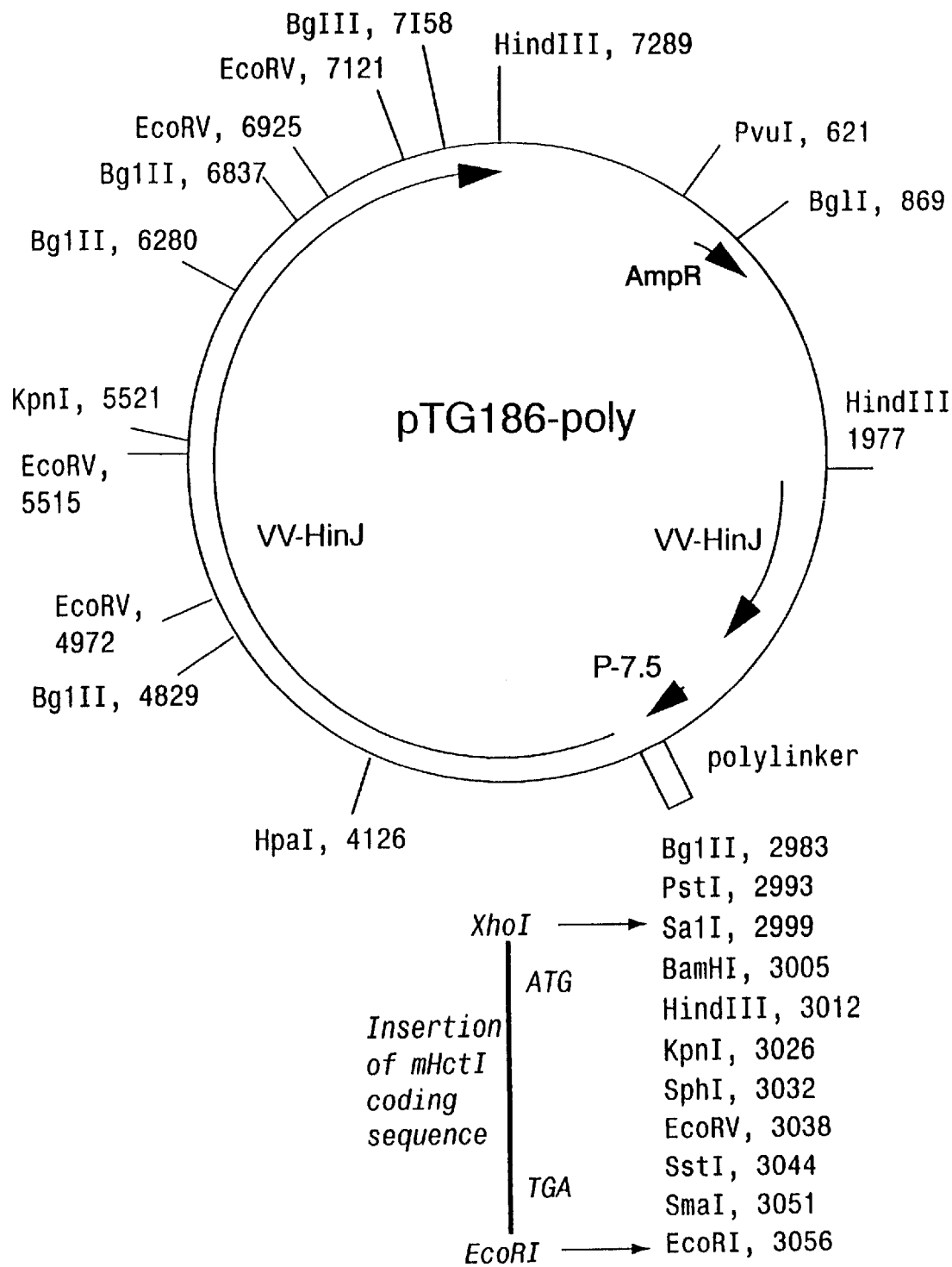

FIG. 7 illustrates Southern blot analyses of mouse genomic DNA using (a) a full length mouse Hct-1cDNA clone and (b) rat genomic DNA probed with clone 14.5a, FIG. 8 illustrates a genomic map of mouse Hct-1, FIG. 9 illustrates a partial nucleotide sequence of human genomic Hct-1 (CYP7B1) and the encoded polypeptide, FIG. 10 illustrates an amino acid alignment of mouse Hct-1 and human C6YP7, FIG. 11A illustrates Kozak sequences in mRNAs for steroidogenic P540's, FIG. 11B illustrates mutagenesis of the 5'end of the mouse Hct-1 cDNA to sreate a near-consensus translation initiation region surrounding the ATG (AUG), FIG. 12 illustrates yeast expression vectors containing the mouse Hct-1 coding sequence, and FIG. 13 illustrates a vaccinia expression vectors containing the mouse Hct-1 coding sequence.

DESCRIPTION OF SPECIFIC EMBODIMENTS

Details of the isolation of hippocampus-associated DNA molecules according to the invention will now be described by way of example:

1. ISOLATION OF GENE ENCODING RAT HCT-1

1.1 Differential screening of a rat hippocampus cDNA library

To identify genes whose expression is enriched in the hippocampal formation we performed a differential hybridization screen of a hippocampal cDNA library. Adult rat hippocampal RNA was reverse transcribed using a oligo-dT-NotI primer, converted to double-stranded cDNA, EcoRI adaptors were attached and the cDNA's were inserted between the EcoRI and NotI sites of a bacteriophage lamda vector.

1.1.1 Preparation of cDNA libraries

Following anaesthesia (sodium pentobarbital) of adult rats (Lister hooded) the hippocampal formation was dissected, including areas CA1–3 and dentate gyrus, subiculum, alvear and fimbrial fibres but excluding fornix and afferent structures such as septum and entorhinal cortex. Remainder of brain was also pooled taking care to exclude hippocampal tissue. Total RNAs were prepared by a standard guanidinium isothiocyanate procedure, centrifugation through a CsCI cushion, and poly-A$^+$ mRNA selected by affinity chromatography on oligo-dT cellulose. First strand cDNA synthesis used a NotI adaptor primer $$[5\text{-dCAATTCGCGGCCGC}(T)_{15}\text{-3'}]$$

and Moloney murine leukemia virus (MMLV) reverse transcriptase; second strand synthesis was performed by RNaseH treatment, DNA polymerase I fill-in and ligase treatment. Following the addition of hemi-phosphorylated EcoRI adaptors (5'-dCGACAGCAACGG-3' and 5'-dAATTCCGTTGCTGTCG-3') and cleavage with NotI the cDNA was inserted between the NotI and EcoRI sites of bacteriophage lambda vector lambda-ZAPII (Stratagene).

1.1.2 Differential hybridization screening

Recombinant bacteriophage plaques were transferred in duplicate to Hybond-N membranes (Amersham), denatured (0.5M NaOH, 1.5M NaCl, 4 min), renatured (1M Tris.HCI pH 7.4, 1.5M NaCl), rinsed, dried and baked (2 h, 80° C.). Hybridization as described (Church et al., Proc. Natl. Acad. Sci. USA (1984), 81 1991–1995) used a radiolabelled probe prepared by MMLV reverse transcriptase copying of polyA$^+$ RNA (from either hippocampus or the remainder of brain) into cDNA in the presence of $\alpha$-$^{32}$P-dCTP and unlabeled dGTP, dATP and dTTP according to standard procedures. Following washing and exposure for autoradiography, differentially hybridizing plaques were repurified. Inserts were transferred to a pBluescript vector either by cleavage and ligation or by using in vivo excision using the ExAssist/SOLR system (Stratagene).

Duplicate lifts from 500,000 plaques were screened with radiolabelled cDNA probes prepared by reverse transcription of RNA from either hippocampus (Hi) or 'rest of brain' (RB). Approximately 360 clones gave a substantially stronger hybridization signal with the Hi probe than with the RB probe; 49 were analysed in more depth, In vivo excision was used to transfer the inserts to a plasmid vector for partial DNA sequence studies. Of these, 21 were novel (not presented here); others were known genes whose expression is enriched in hippocampus but not specific to the formation (eg., the rat amyloidogenic protein. Northern analysis was first performed using radiolabelled probes corresponding to the 21 novel sequences. While three (12.10a, 14.5a and 15.13a) identified transcripts specific to the hippocampus, 12.10a and 15.13a both hybridized to additional transcripts whose expression was not restricted to the formation. Clone 14.5a appeared to identify transcripts enriched in hippocampus and was dubbed Hct-1.

1.2 Characterisation of Rat Hct-1

1.2.1 Rat Hct-1 encodes a cyto chrome P450

To extend this characterization, the insert of clone 14.5a (300 nt) was used to rescreen the hippocampal cDNA library. 4 positives were identified (clones 14.5a-5, -7, -12 and -13), and the region adjacent to the poly-A tail analysed by DNA sequencing. While clones 5 (0.7 kb) and 12 (1.4 kb) had the same 3' end as the parental clone, clone 7 (0.9 kb) had a different 3' end consistent with utilization of an alternative polyadenylation site. Clone 13 (2.5 kb), however, appeared unrelated to Hct-1 and was dubbed Hct-2.

Clones 12 and 7 were then fully sequenced and the sequences obtained were compared with the database. Significant homology was detected between clone 12 and the human and rat cDNA's encoding cholesterol 7α-hydroxylase, though the sequences are clearly distinct. At the nucleic acid level, the 1428 nt cDNA clone for rat Hct-1 shared 55% identity over an 1100 nt overlap with human cholesterol 7α-hydroxylase (CYP7) and 54% identity over a 1117 nt overlap with rat CYP7. FIG. 1 gives the partial cDNA sequences of rat Hct-1 and the encoded polypeptide.

1.2.2 Hct-1 mRNA expression in rat

Rat Hct-1 clone 14.5a/12 (1.4 kb) was used to investigate the expression of Hct-1 mRNA in rat brain and other organs. We first performed in situ hybridization to sections of rat brain. While these preliminary experiments did not permit unambiguous localization of Hct-1 transcripts, we confirmed expression in the hippocampus, predominantly in the cell layers of the dentate gyrus, while weaker expression was detected in other hippocampal and brain regions (not presented). Northern analysis was then performed on RNA prepared from different sections of rat brain. In FIG. 2A the Hct-1 probe identifies three transcripts in hippocampus of 5.0, 2.1 and 1.8 kb, with the two smaller transcripts being particularly enriched in hippocampus. The larger transcript was only detectable in brain, while the two smaller transcripts were also present in liver (and, at much lower levels, in kidney) but not in other organs tested including adrenal (not shown), testis, and ovary. In brain, expression was also detected in olfactory bulb and cortex while very low levels were present in cerebellum (FIG. 2A).

1.2.3 Sexual dimorphism of Hct-1 expression in liver but not in brain

The expression of several CYPS is known to be sexually dimorphic in liver. We therefore inspected liver and brain of male and female rats for the presence of Hct-1 transcripts. In FIG. 2B the Hct-1 probe revealed the 1.8 and 2.1 kb (and 5.0 kb, Hct-2) transcripts in both male and female brain, with the 2.1 kb Hct-1 transcript predominating. Levels of Hct-1 mRNA's in liver were reduced greater than 20-fold over those detected in brain. Furthermore, Hct-1 transcripts were only significant in liver from male animals; expression of Hct-1 in females was barely detectable demonstrating that hepatic expression of Hct-1 is sexually dimorphic.

2. ISOLATION OF MOUSE HCT-1

2.1 Isolation of mouse Hct-1 cDNA clones

A mouse liver cDNA library, established as NotI-EcoRI fragments in a lambda-gt10 vector, was probed using a rat Hct-1 probe. The library was a kind gift of B. Luckow and K. Kästner, Heidelberg.

Because the transcripts identified by the Hct-1 probe (predominantly 1.8 and 2.1 kb) are clearly longer than the longest cDNA clone (1.4 kb) obtained from our rat hippocampus library, we therefore elected to pursue studies with the mouse Hct-1 ortholog. A mouse liver cDNA library was screened using a rat Hct-1 probe and four clones were selected, none containing a poly-A tail. Two (clones 33 and 35, both 1.8 kb) gave identical DNA sequences at both their 5' and 3' ends, and this sequence was approximately 91% similar to rat Hct-1. The remaining two clones, 23 and 40, were also identical to each other and were related to the other clones except for a 5' extension in (59 nt) and a 3' deletion (99 nt). The complete DNA sequences of clones 35 and 40 were therefore determined.

The sequences obtained were identical throughout the region of overlap. The mouse Hct-1 open reading frame (ORF) commences with a methionine at nucleotide 81 (numbering from clone 40) and terminates with a TGA codon at nucleotide 1600, encoding a protein of 507 amino acids (FIG. 3). At the 5' end it is of note that the ATG initiation codon leading the ORF does not correspond to the translation initiation consensus sequence YYAYYATGR. However, the 5' untranslated region cloned is devoid of other possible initiation codons and an in-frame termination triplet (TAA) lies 20 codons upstream of the ATG. The encoded polypeptide sequence aligns well with other cytochrome P450 sequences and we surmise that the ATG at position 81 represents the correct start site for translation. At the 3' end the truncation of clone 40 lies entirely in the non-coding region downstream of the stop codon. Neither clone contained a poly-A tail but both contained a potential polyadenylation sequence (AATAAA) at a position corresponding precisely to that seen in the rat cDNA.

2.2 Structure of mouse Hct-1 polypeptide

As anticipated, nucleotide sequence homology of mouse Hct-1 was highest with human cholesterol 7a-hydroxylase, with approximately 56% identity over the coding region. At the polypeptide level the mouse ORF shows 81% identity to the rat Hct-1 polypeptide over 414 amino acids; the precise degree of similarity may be different as the full protein sequence of rat Hct-1 is not known. Both the human (CYP7) and rat cholesterol 7a-hydroxylase polypeptides share 39% amino acid sequence identity to mouse Hct-1. FIG. 4A presents the alignment of mouse Hct-1 polypeptide with human CYP7.

The N-terminus of the Hct-1 polypeptide is hydrophobic, a feature shared by microsomal CYP's. This portion of the polypeptide is thought to insert into the membrane of the endoplasmic reticulum, holding the main bulk of the protein on the cytoplasmic side. Consistent with microsomal CYP's, the N-terminus lacks basic amino acids prior to the hydrophobic core (amino acids 9–34).

Several alignment studies have previously highlighted conserved regions within CYP polypeptides. We therefore inspected the Hct-1 sequence for these conserved regions. CYP's contain a highly conserved motif, FxxGxxxCxG (xxxA), present in 202 of the 205 compiled sequences (Nelson et al., supra), that is thought to represent the heme binding site. The arrangement of amino acids around the cysteine residue has been postulated to preserve the three-dimensional structure of this region for ligand binding. This motif is fully conserved in Hct-1 (FIG. 4B). A second conserved domain is also present in CYP's responsible for steroid interconversions. While this domain is largely conserved in Hct-1 an invariant Pro residue is replaced, in Hct-1, by Val (FIG. 4C); the rat Hct-1 polypeptide also contains a Val residue at this position.

2.3 Expression pattern of mouse Hct-1

To verify enriched expression of Hct-1 in hippocampus we performed Northern and in situ hybridization analyses on mouse material. In contrast to the situation in rat, the 1.4 kb clone 12 detected only a 1.8 kb transcript; the 2.1 kb and 5.0 kb transcripts were absent from all tissues examined (FIG. 2C). The apparent absence of the 2.1 kb transcript may only reflect a lower abundance of this transcript because at least some mouse cDNA clones extend beyond the upstream polyadenylation site which is thought, in rat, to generate the shorter (1.8 kb) transcript.

To refine this analysis, a 42-mer oligonucleotide was designed according to the DNA sequence of the 3' untranslated region of the cDNA clone upstream of the first polyadenylation site (materials and methods), so as to minimize cross-hybridization with other CYP mRNA's. Coronal sections of mouse brain were hybridized to the $^{35}$S-labelled probe and, after emulsion dipping, exposed for autoradiography (FIG. 5). Transcripts were detected throughout mouse brain, with no evidence of restricted expression in the hippocampus (FIG. 5A,B). Strongest expression was observed in the corpus callosum, the anterior commisure and fornix while, as in rat, hippocampal expression was particularly prominent in the dentate gyrus (FIG. 5C). Moderate expression levels, comparable to those observed in hippocampus, were observed in cerebellum, cortex and olfactory bulb.

2.4 The structure of the mHct-1 gene.

The use of homologous recombination to manipulate the mouse Hct-1 gene requires knowledge of the intron-exon structure of the gene. Sequences upstream of the first Hct-1 exon could also be analysed for elements which contribute to the transcriptional regulation of Hct-1 expression. For these reasons, the organisation of the mouse Hct-1 gene was investigated.

To assess the complexity of the Hct-1 gene in the genome, that is, whether The Hct-1 gene is present as a single copy in the haploid mouse genome, and to assist in mapping of mHct-1 phage clones, the 1.8 kb full length mouse Hct-1 clone was $^{32}$P-labelled by random primer labelling and used as a probe on a Southern blot of mouse genomic DNA (FIG. 7(a)). Under high stringency conditions the Hct-1 probe recognised a small number of bands within the mouse genomic digests, suggesting that Hct-1 is present in the mouse genome as a single copy gene. To confirm this, the original 0.3 kb cDNA clone, 14.5a, was used to probe a rat genomic Southern blot. The smaller probe hybridised to a single band in BamHI-, EcoRI-, and XbaI -digested genomic rat DNA (FIG. 7(b)).

A mouse genomic DNA library (a gift from A. Reaume, Toronto) prepared from ES cells derived from the 129 mouse strain was screened for genomic clones containing mHct-1 exonic sequence. 750,000 recombinant phage of the lambda DASH II library were plated at a density of 50,000 recombinants per 15 cm plate. Duplicate lifts were made and probed with the 1.4 kb rat Hct-1 clone. After the primary screen, 5 clones were isolated. After secondary screening, three of these phage clones were positive and were purified.

Small scale phage DNA was prepared from each phage lysate and cut with NotI to release the inserts. No internal NotI sites were found in any of the clones. Clone 1-2 contained a 14 kb insert; clone 1-6 contained a 15 kb insert, and clone 1-11 contained a 12 kb insert.

These phage clones were mapped by a combination of restriction enzymes which either cut the lambda clones rarely, or by using restriction sites found in the mHct-1 cDNA sequence (FIG. 3). A 5' probe was created using a 200 bp fragment from the 5' end of mHct-1 cDNA as a probe; this segment extended from the internal BamHI site to an EcoRI site located in the polylinker. The 200 bp 3' cDNA probe extended from the SacI site to the polylinker NotI site. Exon-intron boundaries were determined by subcloning of exon-containing genomic DNA fragments and sequencing (FIG. 8).

Phage clones 1-6 and 1-11 represented 20 kb of contiguous sequence of the Hct-1 locus. 1-2 does not overlap with 1-6 or 1-11, thus the map of the Hct-1 gene in mouse is incomplete. However, the present map shows that mHct-1 spans at least 25 kb of the genome. At least two exons are contained within 1-6. The first exon (referred to as exon II) contains 133 bp of coding sequence, followed by exon III, located 4.0 kb downstream. The 3' boundary of this latter exon is not defined, however approximately 400 bp downstream of its 3' boundary commences exon IV, which together comprise 797 bp of coding sequence. Exon III and IV are also represented in the overlapping sequence of 1-11. A fourth exon of at least 345 bp was identified in 1–2 (referred to as exon VI). The 3' boundary of this exon has not been identified, thus it is not known whether this contains the remaining coding sequence or if there are additional exons.

The following Table provides a summary of the exon-intron structure of Hct-1 (incomplete) and comparison to human CYP7 gene structure. * indicates that these exons are not cloned and are not necessarily one exon. ** indicates that the 3' boundary of exon VI is not confirmed and may not necessarily be the final exon.

| Exon | cDNA sequence represented | exon size (bp) | CYP7 exon (bp) |
|------|---------------------------|----------------|----------------|
| I*   | 1–142                     | 142            | 144            |
| II   | 143–275                   | 133            | 241            |
| III  | 276–?                     | 797            | 587            |
| IV   | ?–1072                    | "              | 131            |
| V*   | 1073–1246                 | 174            | 176            |
| VI** | 1247–(1821)               | (575)          | 1596           |

As shown in the Table, cDNA sequence from nucleotides 1073–1246 is not represented in the identified exons and must be represented in a separate exon. 142 bp of 5' sequence and 227 bp of 3' sequence have not yet been located in the genomic clones. The remaining 5' sequence is most likely contained in one exon, as the 5' probe (BamHI fragment) consistently recognised two bands by Southern analysis (one of which is exon II sequence). The remaining 3' sequence has not been located and may be part of exon VI or be encoded by a separate exon.

3. ISOLATION OF HUMAN GENOMIC SEQUENCES FOR HCT-1

3.1 Conservation of Hct-1 in humans.

The evolutionary conservation of a gene supports a functionally significant role for that gene in the organism. The conservation of Hct-1 in rodents has been demonstrated by the cloning of the rat and mouse cDNAs for Hct-1. To establish the presence of the Hct-1 gene in the human genome, Southern blotting of human DNA was performed. The rat 1.4 kb clone of Hct-1 was used as a radiolabelled probe and gave strong signals from all three species (FIG. 6). A number of hybridising fragments appear to be conserved between species, suggesting conservation of the Hct-1 gene structure. There is a conserved 1.4 kb HindIII band between mouse and rat, while human DNA contains a slightly larger HindIII band of 1.6 kb. Also an EcoRI fragment of 11 kb is conserved in human and rat Hct-1. Conservation of Hct-1 gene structure is also supported from the cDNA digestion patterns of mouse and rat (see FIGS. 6 and 7), where the SacI, HindIII and PstI sites are conserved between the rodent species.

3.2 A single gene for Hct-1 in mouse, rat and human

Because CYP's comprise a family of related enzymes we wished to determine whether close homologs of Hct-1 are present in the mammalian genome. The rat Hct-1 probe (1.4 kb) was used to probe a genomic Southern blot of rat, mouse and human DNA. In FIG. 6 the probe revealed a simple pattern of cross-hybridizing bands in all DNA's examined. In BamHI-cut human DNA only a single major cross-hybridizing band (4 kb) was detected (FIG. 6), while reprobing with the 300 nt. clone 14-5a yielded, in each lane, a single cross-hybridizing band (not shown). These data argue that a single conserved Hct-1 gene is present in mouse, rat and human, and that the mammalian genome does not contain very close homologs of Hct-1 that would be detected by cross-hybridization (>70–80% homology).

3.3 Isolation of sequences encoding human Hct-1

The rat cDNA clone 14.5a-12 was used to probe a Southern blot of human genomic DNA digested with BamHI according to standard procedures. A single band at 3.8 kb was identified that cross-hybridises with the probe. Accordingly, 20 μg of human genomic DNA was cleaved to completion with BamHI, resolved by agarose gel electrophoresis, and the size range 3.4–4.2 kb selected by reference to markers run on the same gel. The gel fragment was digested by agarase treatment, DNA was purified by phenol extraction and ethanol precipitation, and ligated into BamHI-cut bacteriophage lambda ZAP vector (Stratagene). Following packaging in vitro and plating on a lawn of E. coli strain XL1-Blue , plaque lifts of 100,000 clones were screened for hybridisation to the rat cDNA. 12 positive signals were identified and all contained a 3.8 kb insert. One was selected and the segment was partially sequenced, identifying two regions of high homology to the rat (and mouse) cDNA's and corresponding to exons 3 and 4. FIG. 9 presents the nucleotide sequence and FIG. 10 compares the human Hct-1 translation product with the cognate mouse polypeptide.

To extend this characterisation, the 3.8 kb BamHI fragment obtained from the size-selected library was used to screen a genomic library of human DNA prepared by partial Sau3A cleavage and insertion of 14–18 kb fragments into a bacteriophage lambda vector according to standard techniques (gift of Dr. P. Estibeiro, CGR). Positive clones were obtained, and restriction mapping of one confirmed that it contains approximately 14 kb of human DNA encompassing the exons identified above and further regions of the Hct-1 gene; together the different aenomic clones are thought to encompass the entire Hct-1 gene. The human genomic sequence may be used to screen human cDNA libraries for full length cDNA clones; alternatively, following complete DNA sequence determination the human genomic sequence may be expressed in mammalian cells by adjoining it to a suitable promoter sequence and cDNA prepared from the correctly spliced mRNA product so produced. Finally, the genomic Hct-1 sequence would permit the entire coding sequence to be deduced so permitting the assembly of a full length Hct-1 coding sequence by de novo synthesis.

3.4 Expression of Hct-1 protein for enzymatic activity analysis 3.4.1. Expression of Hct-1 polypeptide in yeast cells Recombinant yeast strains are useful vehicles for the production of heterologous cytochrome P450 proteins. It would be possible to express any of the mammalian Hct-1's in yeast, but for simplicity we selected the mouse Hct-1 clone 35. To introduce the mouse Hct-1 (mHct-1) coding sequence into yeast the expression vector pMA91 (Kingsman et al., Meth. Enzymol. 185: 329–341, 1990) was employed. The unique Bglll site in pMA91 was converted to a NotI site by inserting the oligonucleotide 5'GATCGCG-GCCGC3' according to standard procedures. Following cleavage of the resulting plasmid (pMA9 1 -Not) with NotI the mHct-1 cDNA clone 35 was introduced, placing mHct-1 expression under the control of the yeast PGK (phosphoglycerokinase) promoter for high level expression in yeast cells (FIG. 12A). A similar construct utilising the mHct-1 cDNA clone 35 is depicted in FIG. 12B. Expression of mHct-1 in yeast using these plasmid permits the purification of the protein and determination of substrate specificity.

3.4.2. Expression of Hct-1 polypeptide in vaccinia virus

Expression in vaccinia virus is a routine procedure and has been widely employed for the expression of heterologous cytochromes P450 in mammalian cells, including HepG2 and Hela cells (Gonzalez, Aoyama and Gelboin, Meth. in Enzymol. 206: 85–92, 1991; Waxman et al., Archives Biochem. Biophys 290, 160–166,1991). Accordingly we selected plasmid pTG186-poly (Lathe et al., Nature 326, 878–880, 1987) as the transfer/expression vector, although other similar vectors are widely available and may also be employed.

To demonstrate the expression of mammalian Hct-1's in vaccinia virus, for simplicity we selected the mHct-1 clone 35. Similar techniques are applicable to rat and human Hct-1's. To enhance expression we elected to modify the 5' end to conform better to the translation consensus for mammalian cells (YYAYYATGR) though this modification may not be essential.

Accordingly, two oligonucleotides were designed corresponding to the 5' and 3' regions of the mouse cDNA.

The 5' oligonucleotide:

(5'-GGCCCTCGAGCCACCATGCAGGGGAGCCACG-3')

is homologous to the region surrounding the translation initiation site but converts the sequence immediately prior to the ATG to the sequence CCACC; in addition, the oligonucleotide contains a XhoI restriction site for subsequent cloning. The 3' oligonucleotide (GGCCGAATTCTCAGCTTCTCCAAGAA) was chosen according to the sequence downstream of the translation stop site and contains, in addition, an EcoRI site for subsequent cloning. These oligonucleotides were employed in polymerase chain reaction (PCR) amplification through 5 cycles on the clone 35 template; the products were applied to an agarose gel and the desired product band at 1.65 kb was cut out and extracted by standard procedures.

Following cleavage with XhoI and EcoRI the modified fragment was introduced between the EcoRI and SalI sites of pTG186-poly, generating pVV-mHct-1. Recombinational exchange was used to transfer the expression vector to the vaccinia virus genome according to standard procedures, generating VV-mHct-1, as depicted in FIG. 13. This recombinant will permit the expression of high levels of mHct-1 and the identification of the substrate specificity of the protein, as well as the production of antibodies directed against mHct-1.

To identify the product of P450-mediated metabolism, microsomes may easily be prepared (Waxman, Biochem. J. 260: 81–85, 1989) from vaccinia-infected cells: these are incubated with labelled precursors, eg. steroids, and the product identified by thin layer chromatography according to standard procedures (Waxman, Methods in Enzymology 206:462–476).

The Hct-1 provided according to this invention thereby provides a route for the large-scale production of the product described above, for instance a modified steroid, by expressing the P450 in a recombinant organism and supplying the substrate for conversion. It will also be possible to engineer recombinant yeast, for instance, to synthesise the substrate for the Hct-1 P450 in vivo, so as to allow production of the Hct-1 product from yeast supplied with a precursor, for instance cholesterol or other molecule, if that yeast is engineered to contain other P450's or modifying enzymes. It may be possible for Hct-1 to act on endogenous sterols and steroids in yeast to yield product.

Finally, the Hct-1 product may be part of a metabolic chain, and recombinant organisms may be engineered to contain P450's or other enzymes that convert the Hct-1 product to a subsequent product that may in turn be harvested from the organism.

4. DISCUSSION

In experiments to characterize transcripts enriched in the hippocampal formation we isolated cDNA clones corresponding to Hct-1 (hippocampal transcript) from a library prepared from rat hippocampus RNA. In rat, expression appeared to be most abundant in hippocampus with some expression in cortex and substantially less expression other in brain regions. Elsewhere in the body transcripts were only detected in liver and, to a lesser extent, in kidney; expression was barely de tect able in ovary, testis and adrenal, also sites of steroid transformations. Hepatic expression was sexually dimorphic with Hct-1 mRNA barely detectable in female liver. In rat brain and liver, Hct-1 identifies two transcripts of 1.8 and 2.1 kb that appear to be generated by alternative polyadenylation; a 5.0 kb transcript weakly detected in brain is thought not to originate from the Hct-1 gene but instead encodes a polypeptide related to the GTPase activating protein, ABR (active BCR-related).

Sequence analysis of Hct-1 cDNA clones revealed an extensive open reading frame encoding a protein with homology to cytochromes P450 (CYP's), a family of heme-containing mono-oxygenases responsible for a variety of steroid and fatty acid interconversions and the oxidative metabolism of xenobiotics. Although the mouse cDNA coding region appears complete, the absence of a consensus translation initiation site flanking the presumed initiation codon could indicate that Hct-1 polypeptide synthesis is subject to regulation at the level of translation initiation.

Homology was highest with rat and human cholesterol 7α-hydroxylase, known as CYP7. While related, Hct-1 is clearly distinct from CYP7, sharing only 39% homology over the full length of the protein. CYP polypeptides sharing greater than 40% sequence identity are generally regarded as belonging to the to the same family, and Hct-1 and CYP7 (39% similarity) are hence borderline. The conservation of other unique features between Hct-1 and CYP7 however argues for a close relationship and Hct-1 has been provisionally named 'CYP7B' by the P450 Nomenclature Committee (D. R. Nelson, personal communication).

From the Hct-1 leader sequence we surmise that the Hct-1 polypeptide resides, like CYP7, in the endoplasmic reticulum and not in mitochondria, the other principal cellular site of CYP activity. The strictly conserved heme binding site motif FxxGxxxCxG(xxxA) is clearly present in Hct-1 (residues 440–453). It is of note that the 'steroidogenic domain', conserved in many CYP's responsible for steroid interconversions, is also present in Hct-1 (amino acids 348–362), except that a consensus Pro residue is replaced by Val in both the mouse and rat Hct-1 polypeptides. Of previously known 34 CYP sequences, only 4 contain an amino acid residue other than Pro at this position. Whereas 2 of these harbour an unrelated amino acid (Glu; CYP3A1, CYP3A3), interestingly, a Val residue is present in bovine CYP17 (steroid 17a-hydroxylase, 44) at a position equivalent to that in Hct-1 while human CYP17 harbours a conservative substitution at this site (Leu; 44). Despite this similarity, however, the overall extent of homology between Hct-1 and CYP17 (22.5%, not shown) is lower than with CYP7 (39%).

Neither Hct-1 and CYP7 appear to contain a conserved $O_2$ binding pocket (equivalent to residues 285–301 in Hct-1). Crystallographic studies on the bacterial CYP1O1 indicated that a Thr residue (corresponding to position 294 in Hct-1) disrupts helix formation in that region and is important in providing a structural pocket for an oxygen molecule. Site-directed mutagenesis of this Thr residue in both CYP4A1 and CYP2C11 demonstrated that this region can influence substrate specificity and affinity. In both Hct-1 and CYP7 the conserved Thr residue is replaced by Asn. This modification suggests that Hct-1 and CYP7 are both structurally distinct from other CYP's in this region; this may be reflected both in modified oxygen interaction and substrate choice.

The sexual dimorphism of Hct-1 expression observed in rat resembles that observed with a number of other CYP's. CYP2C12 is expressed preferentially in liver of the female rat while, like Hct-1, CYP2C11 is highly expressed in male liver but only at low levels in the female tissue. This dimorphic expression pattern of CYP2C family members is thought to be determined by the dimorphism of pulsatility of growth hormone secretion. Brain expression of Hct-1 is not subject to this control suggesting that regulatory elements determining Hct-1 expression in brain differ from those utilized in liver. However, we have not examined species other than rat; it cannot be assumed that the same regulation will exist in other species. Indeed, sexually dimorphic gene expression is not necessarily conserved between different strains of mouse.

Expression of Hct-1 was widespread in mouse brain. The expression pattern was most consistent with glial expression but further experiments will be required to compare neuronal and non-neuronal levels of expression. In mouse brain only the 1.8 kb transcript was detected, though cDNA's were obtained corresponding to transcripts extending beyond the first polyadenylation site; such extended transcripts are thought to give rise to the 2.1 kb transcript in rat. This suggests the downstream polyadenylation site seen in rat Hct-1 is under-utilized in mouse Hct-1 or absent. While in situ hybridization studies of Hct-1 in rat brain were inconclusive, a difference in expression pattern between mouse and rat appears likely; further work will be required to confirm this. However, such a difference would be unsurprising because cytochromes P450 are well known to vary widely in their level and pattern of expression in different species; for instance, hepatic testosterone 16-hydroxylation levels differ by more than 100-fold between guinea pig and rat.

Our data indicate that the Hct-1 gene is present in rat, mouse and human, and there appear to be no very close relatives in the mammalian genome. While CYP genes are scattered over the mouse and human genomes, CYP subfamilies can cluster on the same chromosome. For instance, the human CYP2A and 2B subfamily genes are linked to chromosome 19, CYP2C and 2E subfamilies are located on human chromosome 10, and the mouse cyp2a, 2b and 2e subfamilies are present on mouse chromosome 7. The gene encoding human cholesterol 7α-hydroxylase (CYP7) is located on chromosome 8q11-q12.

Together our data argue that Hct-1 and CYP7 are closely related: this suggests that the substrate for Hct-1, so far unknown, is likely to be related to cholesterol or one of its steroid metabolites. This interpretation is borne out by the presence, in Hct-1, of the steriodogenic domain conserved in a number of steroid-metabolizing CYP's. While experiments are underway to determine the substrate specificity of Hct-1, the possibility that Hct-1 acts on cholesterol or its steroid metabolites in brain is of some interest. CYP7 (cholesterol 7α-hydroxylase) is responsible for the first step in the metabolic degradation of cholesterol. This is of note in view of the association of particular alleles of the APOE gene encoding the cholesterol transporter protein apolipoprotein E with the onset of Alzheimer's disease, a neurodegenerative condition whose cognitive impairments are associated with early dysfunction of the hippocampus.

What role might Hct-1 play in the brain? In the adult CYP's are generally expressed abundantly in liver, adrenal and gonads, while the level of CYP activity in brain is estimated to be 0.3 to 3% of that found in liver (see 58). Because levels of Hct-1 mRNA expression in rat and mouse brain far exceed those in liver it could be argued that the primary function of Hct-1 lies in the central nervous system. The documented ability of cholesterol-derived steroids to interact with neurotransmitter receptors and modulate both synaptic plasticity and cognitive function suggests that Hct-1 and its metabolic product(s) may regulate neuronal function in vivo.

5. SUMMARY

Hct-1 (hippocampal transcript) was detected in a differential screen of a rat hippocampal cDNA library. Expression of Hct-1 was enriched in the formation but was also detected in rat liver and kidney, though at much lower levels; expression was barely detectable in testis, ovary and adrenal. In liver, unlike brain, expression was sexually dimorphic: hepatic expression was greatly reduced in female rats. In mouse, brain expression in was widespread, with the highest levels being detected in corpus callosum; only low levels were detected in liver. Sequence analysis of rat and mouse Hct-1 cDNAs revealed extensive homologies with cytochrome P450's (CYP's), a diverse family of heme-binding monooxygenases that metabolize a range of substrates including steroids, fatty acids and xenobiotics. Among the CYP's, Hct-1 is most similar (39% at the amino acid sequence) to cholesterol 7α-hydroxylase (CYP7), and contains the diagnostic steriodogenic domain present in other steriod-metabolizing CYPs, but clearly represents a type of CYP not previously reported. Genomic Southern analysis indicates that a single gene corresponding to Hct-1 is present in mouse, rat and human. Hct-1 is unusual in that, unlike all other CYP's described, the primary site of expression is in the brain. Similarity to CYP7 and other steroid-metabolizing CYP's argues that Hct-1 plays a role in steroid metabolism in brain, notable because of the documented ability of brain-derived steroids (neurosteroids) to modulate cognitive function in vivo.

6. DETAILS OF EXPERIMENTAL PROTOCOLS

Northern analysis—Total RNA was extracted by tissue homogenization in guanidinium thiocyanate according to a standard procedure and further purified by centrifugation through a CsCl cushion. Where appropriate, polyA-plus RNA was selected on oligo-dT cellulose. Electrophoresis of RNA (10 μg) on 1% agarose in the presence of 7% formaldehyde was followed by capillary transfer to nylon membranes, baking (2 h, 80° C.), and rinsing in hybridization buffer (0.25M NaPhosphate, pH 7.2; 1 mM EDTA, 7% sodium dodecyl sulphate [SDS], 1% bovine serum albumin) as described (Church et al., supra). Probes were prepared by random-priming of DNA polymerase copying of denatured double-stranded DNA. Hybridization (16 h, 68° C.) was followed by washing (3 times, 20 mM NaPhosphate pH 7.2, 1 mM EDTA, 1%, SDS, 20 min.) and membranes exposed for autoradiography. The loading control probe was a 0.5 kb cDNA encoding the ubiquitously expressed rat ribosomal protein S26.

In situ hybridization—Synthetic Hct-1 oligonucleotide probes 5'-dGACAGGTTTTGTGACCCAAAACAAACTGGA TGGATCGCAATC-3' (rat, 55% G+C) and 5'-ATCACGGAGCTCAGCACATGCAGCCTTACTCTG CAAAGCTTC-3' (mouse—48% G+C) were labelled using terminal transferase (Boehringer Mannheim) and $\alpha$-$^{35}$-dATP (Amersham) according to the manufacturer's instructions. The control probe, 5'-dAGCCTTCTGGGTCGTAGCTGACTCCTGCTGCT GAGCTGCAACAGCTTT-3' (56% G+C) was based on human opsin cDNA. Frozen coronal 10 μm sections of brain were fixed (4% paraformaldehyde, 10 min), rinsed, treated with proteinase K (20,μg/ml in 50 mM Tris.HCl, pH 7.4, 5 mM EDTA, 5 min), rinsed, and refixed with paraformaldehyde as before. Following acetylation (0.25% acetic anhydride, 10 min) and rinsing, sections were dehydrated by passing though increasing ethanol concentrations (30, 50, 70, 85, 95, 100, 100%, each for 1 minute except the 70% step [5 min]). Following CHCl$_3$ treatment (5 min), and rinsing in ethanol, sections were dried before hybridization. Hybridization in buffer (4×standard saline citrate [1×SSC= 0.15M NaCl, 0.015M Na$_3$citrate], 50% v/v formamide, 10% w/v dextran sulphate, 1× Denhardt's solution, 0.1% SDS, 500 μg/ml denatured salmon sperm DNA, 250 μg/ml yeast tRNA) was for 16 h at 37° C. Slides were washed (4×15 min., 1×SSC, 60° C.; 2×30 min., 1×SSC, 20° C.), dipped into photographic liquid emulsion (LM-1, Amersham), exposed and developed according to the manufacturer's specifications. Slides were counterstained with 1% methyl green.

Southern hybridization—Genomic DNA prepared from mouse or rat liver, or from human lymphocytes, was digested with the appropriate restriction endonuclease, resolved by agarose gel electrophoresis (0.7%) and transferred to Hybond-N membranes. Following baking (2 h, 80° C.), hybridization conditions were as described for Northern analysis.

Hybridisation Conditions. Hybridisation conditions used were based on those described by Church and Gilbert, Proc. Natl. Acad. Sci. USA (1984) 81, 1991–1995.

1. Filters were pre-wet in 2XSSC.
2. The hybridisation was performed in a rotating glass cylinder (Techne Hybridiser ovens). 10 ml of Hybridisation Buffer was added to the cylinder with the filter.
3. Prehybridisation and hybridisation were carried out at 68° C. unless otherwise specified.
4. The filters were prehybridised for 30 minutes, after which the probe was added directly and hybridisation proceeded overnight. (Double-stranded probes were denatured by boiling for 2 minutes, then placing on ice).
5. Washes were performed at 68° C. (unless otherwise stated) with 2 changes of Wash Buffer I for 10 minutes each, followed by three changes of Wash Buffer II each for 20 minutes.
6. The filters were blotted dry, but not allowed to dry out, then placed between Saran wrap, and against X-ray film for autoradiography.

Hybridisation Buffer:
0.25M sodium phosphate pH 7.2

1 mM EDTA
7% SDS
1% BSA
Wash Buffer I:
20 mM sodium phosphate pH 7.2
2.5% SDS
0.25% BSA
1 mM EDTA
Wash Buffer II:
20 mM sodium phosphate pH 7.2
1 mM EDTA
1% SDS Screening of Bacteriophage lambda libraries. The rat hippocampus cDNA library was oligo-(dT)-NotI primed and cloned in lambda ZAP II (Stratagene) with an EcoRI adaptor at the 5' end, and was prepared in the lab by Miss M. Richardson and Dr. J. Mason; the mouse liver cDNA library was oligo-(dT)-primed and cloned into lambda gt10 with EcoRI/NotI adaptors, and was a gift from Dr. B. Luckow, Heidelberg; the mouse ES cell genomic library was cloned from a partial Sau3A digest into lambda DASH II (Stratagene), and was a gift from A. Reaume, Toronto.

The libraries were screened as described above by hybridization.

In vivo excision of pBluescript from lambda ZAP II vector was performed using the ExAssist/SOLR system (Stratagene, 200253).

In situ hybridisation. Frozen 10μ coronal sections of rat and mouse brains were provided by Dr. M. Steel.

Hybridisation Conditions All probes were oligonucleotides which were labelled by homopolymer tailing using a-$^{35}$S-dATP and terminal transferase.

The sequences or references of the oligonucleotides used as probes for in situ hybridisation were as follows:

rat Hct-1 (a 45-mer, beginning 26 nt 5' from the polyA tail, nucleotides 1361–1403 in FIG. 4.2) (for relative position in mouse gene, see FIG. 4.3)

5'-GACAGGTTTTGTGACCCAAAACAAACTG-GATGGATCGCAATC-3'

Nathans mouse Hct-1 (nt 1558-1599)

5'-ATCACGGAGCTCAGCACATGCAGCCT-TACTCTGCAAAGCTTC-3' rat clone 13 (a 42-mer, beginning 112 nt 5' from polyA tail)

5'-TATATCCATACCAACTTATTGGGAGTC-CCATCCTACCTCATCAGC-3' rat/mouse muscarinic receptor M1 (Buckley et al., 1988)
rat/mouse opsins (Nathans et al., Science (1986) 232, 193–202)

1. The prepared $^{35}$S-tailed probe (resuspended in 10 mM DTT in TE) was diluted to 2×10$^6$cpm/ml in hybridisation buffer. DTT is also added to this mixture to a final concentration of 50 mM.

2. 100 ml of the probe mixture was carefully layered onto each microscope slide. A piece of parafilm cut to the size of the microscope slide was then layered over the probe mixture, allowing the probe and hybridisation mixture to cover all the sections. Air bubbles under the parafilm were avoided.

3. The slides were placed in a humidified container, sealed, and incubated at 37° C. overnight.

4. After hybridisation, the parafilm was carefully removed using forceps.

5. The slides were placed back in Coplin jars, and the hybridised sections washed in four changes of 1XSSC for 15 minutes at 55° C. or 60° C., and then two changes of 1XSSC for 30 minutes at room temperature.

6. The slides were rinsed briefly in dH$_2$O, then left to air dry.

Hybridisation Buffer*:
4×SSC
50% (v/v) deionised formamide
10% (w/v) dextran sulphate
1× Denhardt's solution
0.1% (w/v) SDS
500 μg/ml ssDNA
250 μg/ml yeast tRNA
*buffer was de-gassed before use

7. FIGURE LEGENDS

FIG. 1. Sequence of partial rat Hct-1 cDNA and the encoded polypeptide.

The nucleotide sequence and translation product of the 1.4 kb cDNA clone 12 including additional clone 7 sequence (lower case). The two putative polyadenylation signals are underlined.

FIG. 2. Northern analysis of Hct-1 expression in adult rat and mouse brain.

Panel A. Expression in rat brain and other tissues; panel B. sexually dimorphic expression in rat liver; panel C. Expression in mouse tissues. Poly-A$^+$ (A) or total (B,C) RNA from organs of adult animals were resolved by gel electrophoresis; the hybridization probe was rat Hct-1 cDNA clone 12 (1.4 kb), the probe for the loading control (below) corresponds to ribosomal protein S26. Tissues analysed are: Hi, hippocampus; RB, remainder of brain lacking hippocampus; Cx, cortex; Cb, cerebellum; Ob; olfactory bulb; Li, liver; He, heart; Th, thymus; Ki, kidney; Ov, ovary; Te, testis; Lu, lung.

FIG. 3. Mouse Hct-1 cDNA and the sequence of the encoded polypeptide.

The restriction map of the cDNA (above) corresponds to the compilation of two independent clones sequenced; the cross-hatched box indicates the coding region. The nucleotide sequence and translation product (below) derives from this compilation. Lower case sequences indicate the 59 additional 5' nucleotides in clone 40 and the 99 additional 3' nucleotides in clone 35. The putative polyadenylation site is underlined.

FIG. 4. Alignment of mouse Hct-1 with human CYP7 (cholesterol 7α-hydroxylase, Noshiro and Okuda, 1990) and other steroidogenic P450s.

Panel A: Identical amino acids are indicated by a bar; hyphens in the amino acid sequences indicate gaps introduced during alignment. The N-terminal hydrophobic leader sequences are underlined. The position of the conserved Thr residue within the O$_2$-binding pocket of other CYP's (43), but replaced by Asn in Hct-1 (position 294) and CYP7, is indicated by an asterisk. Panels B,C: conserved residues in the heme-binding (residues 440-453, B) and steroidogenic (residues 348–362, C) domains conserved between Hct-1 and other similar CYP's (overlined in A). Sequences are human CYP7 (7α-hydroxylase; 37); bovine CYP17 (17a-hydroxylase; 44); human CYP11 B1 (steroid β-hydroxylase; 45); human CYP21B (21 -hydroxylase; 11); human CYP11A1 (P450scc; cholesterol side-chain cleavage; 46); human CYP27 (27-hydroxylase; 47).

FIG. 5. Analysis of Hct-1 expression in adult mouse brain.

The hybridization probe was a synthetic oligonucleotide corresponding to the 3' untranslated region of mouse Hct-1 cDNA. Panel a. coronal section; panel b: coronal section, rostral to a, showing hybridization in corpus callosum, cc; fornix, f; and anterior commissure, ac; panel c: enlargement of section through the hippocampus; DG, dentate gyrus; panel d. section adjacent to the section in a hybridized with an oligonucleotide specific for opsin (negative control).

FIG. 6. Southern analysis of Hct-1 coding sequences in mouse, rat and human

Total DNA was cleaved as indicated with restriction endonucleases B, BamHI; E, EcoRI; H, HindIII; X, XbaI; resolved by agarose gel electrophoresis, and probed with rat Hct-1 cDNA clone 12 before exposure to autoradiography.

FIG. 7 Genomic DNA Southern blot analysis of Hct-1 (a) Mouse genomic DNA probed with the full-length mouse Hct-1 cDNA clone. (b) Rat genomic DNA probed with clone 14.5a (original 0.3 kb clone of rHct-1). 10 μg of genomic DNA was digested with the indicated enzymes.

FIG. 8 Genomic map of mouse Hct-1 (incomplete). Exons II, III, IV and VI are represented on the phage clones (filled boxes). Exons I and V are not located. As indicated in Table 4. 1, the boundaries of exons II, III B (BamHI); H(HindIII); S(SacI); X(XhoI)

```
                                                                SequId No: 1
A  L  E  Y  Q  Y  V  M  K  N  P  K  Q  L  S  F  E  K  F  S
GCCTTGGAGTACCAGTATGTAATGAAAAACCCAAAACAATTAAGCTTTGAGAAGTTCAGC         60

R  R  L  S  A  K  A  F  S  V  K  K  L  L  T  N  D  D  L  S
CGAAGATTATCAGCGAAAGCCTTCTCTGTCAAGAAGCTGCTAACTAATGACGACCTTAGC        120

N  D  I  H  R  G  Y  L  L  L  Q  G  K  S  L  D  G  L  L  E
AATGACATTCACAGAGGCTATCTTCTTTTACAAGGCAAATCTCTGGATGGTCTTCTGGAA        180

T  M  I  Q  E  V  K  E  I  F  E  S  R  L  L  K  L  T  D  W
ACCATGATCCAAGAAGTAAAAGAAATATTTGAGTCCAGACTGCTAAAACTCACAGATTGG        240

N  T  A  R  V  F  D  F  C  S  S  L  V  F  E  I  T  F  T  T
AATACAGCAAGAGTATTTGATTTCTGTAGTTCACTGGTATTTGAAATCACATTTACAACT        300

I  Y  G  K  I  L  A  A  N  K  K  Q  I  I  S  E  L  R  D  D
ATATATGGAAAAATTCTTGCTGCTAACAAAAAACAAATTATCAGTGAGCTGAGGGATGAT        360

F  L  K  F  D  D  H  F  P  Y  L  V  S  D  I  P  I  Q  L  L
TTTTTAAAATTTGATGACCATTTCCCATACTTAGTATCTGACATACCTATTCAGCTTCTA        420

R  N  A  E  F  M  Q  K  K  I  I  K  C  L  T  P  E  K  V  A
AGAAATGCAGAATTTATGCAGAAGAAAATTATAAAATGTCTCACACCAGAAAAGTAGCT        480

Q  M  Q  R  R  S  E  I  V  Q  E  R  Q  E  M  L  K  K  Y  Y
CAGATGCAAAGACGGTCAGAAATTGTTCAGGAGAGGCAGGAGATGCTGAAAAAATACTAC        560

G  H  E  E  F  E  I  G  A  H  H  L  G  L  L  W  A  S  L  A
GGGCATGAAGAGTTTGAAATAGGAGCACATCATCTTGGCTTGCTCTGGGCCTCTCTAGCA        600

N  T  I  P  A  M  F  W  A  M  Y  Y  L  L  Q  H  P  E  A  M
AACACCATTCCAGCTATGTTCTGGGCAATGTATTATCTTCTTCAGCATCCAGAAGCTATG        660

E  V  L  R  D  E  I  D  S  F  L  Q  S  T  G  Q  K  K  G  F
GAAGTCCTGCGTGACGAAATTGACAGCTTCCTGCAGTCAACAGGTCAAAAGAAAGGACCT        720

G  I  S  V  H  F  T  R  E  Q  L  D  S  L  V  C  L  E  S  A
GGAATTTCTGTCCACTTCACCAGAGAACAATTGGACAGCTTGGTCTGCCTGGAAAGCGCT        780

I  L  E  V  L  R  L  C  S  Y  S  S  I  I  R  E  V  Q  E  D
ATTCTTGAGGTTCTGAGGTTGTGCTCCTACTCCAGCATCATCCGTGAAGTGCAAGAGGAT        840

M  D  F  S  S  E  S  R  S  Y  R  L  R  K  G  D  F  V  A  V
ATGGATTTCAGCTCAGAGAGTAGGAGCTACCGTCTGCGGAAAGGAGACTTTGTAGCTGTC        900

F  P  P  M  I  H  N  D  P  E  V  F  D  A  P  K  D  F  R  F
TTTCCTCCAATGATACACAATGACCCAGAAGTCTTCGATGCTCCAAAGGACTTTAGGTTT        960

D  R  F  V  E  D  G  K  K  K  T  T  F  F  K  G  G  K  K  L
GATCGCTTCGTAGAAGATGGTAAGAAGAAAACAACGTTTTTCAAAGGAGGAAAAAAGCTG       1020

K  S  Y  I  I  P  F  G  L  G  T  S  K  C  P  G  R  Y  F  A
AAGAGTTACATTATACCATTTGGACTTGGAACAAGCAAATGTCCAGGCAGATACTTTGCA       1080

I  N  E  M  K  L  L  V  I  I  L  L  T  Y  F  D  L  E  V  I
ATTAATGAAATGAAGCTACTAGTGATTATACTTTTAACTTATTTTGATTTAGAAGTCATT       1140

D  T  K  P  I  G  L  N  H  S  R  M  F  L  G  I  Q  H  P  D
GACACTAAGCCTATAGGACTAAACCACAGTCGCATGTTTCTGGGCATTCAGCATCCAGAC       1200

S  D  I  S  F  R  Y  K  A  K  S  W  R  S  ***
TCTGACATCTCATTTAGGTACAAGGCAAAATCTTGGAGATCCTGAAAGGGTGGCAGAGAA       1260
```

-continued

```
GCTTAGCGGAATAAGGCTGCACATGCTGAGCTCTGTGATTTGCTGTACTCCCCAAATGCA      1320

GCCACTATTCTTGTTTGTTAGAAAATGGCAAATTTTTATTTGATTGCGATCCATCCAGTT      1380

TGTTTTGGGTCACAAAACCTGTCATAAAATAAAGCGCTGTCATGGTGTaaaaaaatgtca      1440 tggcaatcatttcaggataaggtaaaataacgttttcaagtttgtacttactatgatttt      1500 tatcatttgtagtgaatgtgcttttccagtaataaatttgcgccagggtgattttttta      1560 attactgaaatcctctaatatcggttttatgtgctgccagaaaagtgtgccatcaatgga     1620 cagtataacaatttccagttttccagagaagggagaaattaagccccatgagttacgctg      1680 tataaaattgttctcttcaactataatatcaataatgtctatatcaccaggttacctttg     1740 cattaaatcgagttttgcaaaag 1763
```

```
                                                                        SequID No: 2
        ggcaggcacagcctctggtctaagaagagagggcactgtgcagaagccatcgctccctaC    60
                  M   Q   G   A   T   T   L   D   A   A   S   P   G   P    14
AGAGCCGCCAGCTCGTCGGGATGCAGGGAGCCACGACCCTAGATGCCGCCTCGCCAGGGC           120
  L   A   L   L   G   L   L   F   A   A   T   L   L   L   S   A   L   F   L   L    34
CTCTCGCCCTCCTAGGCCTTCTCTTTGCCGCCACCTTACTGCTCTCGGCCCTGTTCCTCC           180
  T   R   R   T   R   R   P   R   E   P   P   L   I   K   G   W   L   P   Y   L    54
TCACCCGGCGCACCAGGCGCCCTCGTGAACCACCCTTGATAAAAGGTTGGCTTCCTTATC          240
  G   M   A   L   K   F   F   K   D   P   L   T   F   L   K   T   L   Q   R   Q    74
TTGGCATGGCCCTGAAATTCTTTAAGGATCCGTTAACTTTCTTGAAAACTCTTCAAGGC           300
  H   G   D   T   F   T   V   F   L   V   G   K   Y   I   T   F   V   L   N   P    94
AACATGGTGACACTTTCACTGTCTTCCTTGTGGGGAAGTATATAACATTTGTTCTGAACC          360
  F   Q   Y   Q   Y   V   T   K   N   P   K   Q   L   S   F   Q   K   F   S   S    114
CTTTCCAGTACCAGTATGTAACGAAAAACCCAAAACAATTAAGCTTTCAGAAGTTCAGCA           420
  R   L   S   A   K   A   F   S   V   K   K   L   L   T   D   D   D   L   N   E    134
GCCGATTATCAGCGAAAGCCTTCTCTGTAAAGAAGCTGCTTACTGATGACGACCTTAATG          480
  D   V   H   R   A   Y   L   L   L   Q   G   K   P   L   D   A   L   L   E   T    154
AAGACGTTCACAGAGCCTATCTACTTCTACAAGGCAAACCTTTGGATGCTCTTCTGGAAA          540
  M   I   Q   E   V   K   E   L   F   E   S   Q   L   L   K   I   T   D   W   N    174
CTATGATCCAAGAAGTAAAAGAATTATTTGAGTCCCAACTGCTAAAAATCACAGATTGGA          600
  T   E   R   I   F   A   F   C   G   S   L   V   F   E   I   T   F   A   T   L    194
ACACAGAAAGAATATTTGCATTCTGTGGCTCACTGGTATTTGAGATCACATTTGCGACTC         660
  Y   G   K   I   L   A   G   N   K   K   Q   I   I   S   E   L   R   D   D   F    214
TATATGGAAAAATTCTTGCTGGTAACAAGAAACAAATTATCAGTGAGCTAAGGGATGATT          720
  F   K   F   D   D   M   F   P   Y   L   V   S   D   I   P   I   Q   L   L   R    234
TTTTTAAATTTGATGACATGTTCCCATACTTAGTATCTGACATACCTATTCAGCTTCTAA         780
  N   E   E   S   M   Q   K   K   I   I   K   C   L   T   S   E   K   V   A   Q    254
GAAATGAAGAATCTATGCAGAAGAAAATTATAAAATGCCTCACATCAGAAAAAGTAGCTC          840
  M   Q   G   Q   S   K   I   V   Q   E   S   Q   D   L   L   K   R   Y   Y   R    274
AGATGCAAGGACAGTCAAAAATTGTTCAGGAAAGCCAAGATCTGCTGAAAAGATACTATA         900
```

```
         H   D   D   P   E   I   G   A   H   H   L   G   F   L   W   A   S   L   A   N         294
GGCATGACGATTCTGAAATAGGAGCACATCATCTTGGCTTTCTCTGGGCCTCTCTAGCAA                                    960
         T   I   P   A   M   F   W   A   M   Y   Y   I   L   R   H   F   E   A   M   E         314
ACACCATTCCAGCTATGTTCTGGGCAATGTATTATATTCTTCGGCATCCTGAAGCTATGG                                    1020
         A   L   R   D   E   I   D   S   F   L   Q   S   T   G   Q   K   K   G   P   G         334
AAGCCCTGCGTGACGAAATTGACAGTTTCCTGCAGTCAACAGGTCAAAAGAAAGGGCCTG                                    1080
         I   S   V   H   F   T   R   E   Q   L   D   S   L   V   C   L   E   S   T   I         354
GAATTTCAGTCCACTTCACCAGAGAACAATTGGACAGCTTGGTCTGCCTGGAAAGCACTA                                    1140
         L   E   V   L   R   L   C   S   Y   S   S   I   I   R   E   V   Q   E   D   M         374
TTCTTGAGGTTCTGAGGCTGTGCTCATACTCCAGCATCATCCGAGAAGTGCAGGAGGATA                                    1200
         N   L   S   L   E   S   K   S   F   S   L   R   K   G   D   F   V   A   L   F         394
TGAATCTCAGCTTAGAGAGTAAGAGTTTCTCTCTGCGGAAAGGAGATTTTGTAGCCCTCT                                    1260
         P   P   L   I   H   N   D   P   E   I   F   D   A   P   K   E   F   R   F   D         414
TTCCTCCACTCATACACAATGACCCGGAAATCTTCGATGCTCCAAAGGAATTTAGGTTCG                                    1320
         R   F   I   E   D   G   K   K   K   S   T   F   F   K   G   G   K   R   L   K         434
ATCGGTTCATAGAAGATGGTAAGAAGAAAAGCACGTTTTTCAAAGGAGGGAAGAGGCTGA                                    1380
         T   Y   V   M   P   F   G   L   G   T   S   K   C   P   G   R   Y   F   A   V         454
AGACTTACGTTATGCCTTTTGGACTCGGAACAAGCAAATGTCCAGGGAGATATTTTGCAG                                    1440
         N   E   M   K   L   L   L   I   E   L   L   T   Y   F   D   L   E   I   I   D         474
TGAACGAAATGAAGCTACTGCTGATTGAGCTTTTAACTTATTTTGATTTAGAAATTATCG                                    1500
         R   K   P   I   G   L   N   H   S   R   M   F   L   G   I   Q   H   P   D   S         494
ACAGGAAGCCTATAGGGCTAAATCACAGTCGGATGTTTTAGGTATTCAGCACCCCGATT                                     1560
         A   V   S   F   R   Y   K   A   K   S   W   R   S   ***                                 507
CTGCCGTCTCCTTTAGGTACAAAGCAAAATCTTGGAGAAGCTGAAAGTGTGGCAGAGAAG                                    1620
CTTTGCAGAGTAAGGCTGCATGTGCTGAGCTCCGTGATTTGGTGCACTCCCCCAAATGCA                                    1680
ACCGCTACTCTTGTTTGAAAATGGCAAATTTATATTTGGTTGAGATCAATCCAGTTGGTT                                    1740
TTGGGTCACAAAACCTGTCATAAAATAAAGCAGTGTGATGGtttaaaaaatgtcatggca                                    1800
atcatttcaggataaggtaaaataacattttcaagtttgtacttactatgattttttatca                                   1860
tttgtagtgaatgtgctttt                                                                            1880

SequID No: 3.
ggatccaaccaagtttccagatcttataaatgtggtgaatggtgaatgacttcctgaaga                                    60
atggatgaatggatgtgttctagtttggaatcctgtgtcagtcacaagtcaatatgtgac                                    120
cttgaacatgttattaaatctcccacatccataaaagtgaaaatgctggcattagtggat                                    180
ttttgccagtgttgaattagacatttatttgtgagtacctgctccatacagtatggtcat                                    240
ttatttgagttaaaattgttgtatttgaacaaaactcagatgacacctaagcatgaaaaa                                    300
                                                               intron 2
gctctttatgaagtataaatactcagaaatggaatggcatgttgccaatttgttttctgc                                    360
tttattgagggaaatatatgagaagtatttaagtcaggggattatgaggaatatttaaag                                    420
gata(--190nt-)tctagagtgttttccaccatctttcaaaggaaacatgtagtgtacc                                    680
ttcgaatgaaatggatttgtattaaacttttttgccttagttattagggtctttctaattt                                   740
```

```
ttgattaacatatttttttaatttgtggtgtttatttctgttttttattaacaaacgaact     800
                                  GlyLysTyrIleThrPheIleProGlyPro
catatgctcctctctcttttttttttttctGGAAAGTACATAACATTTATACCTGGACCC       860

PheGlnTyrGlnLeuValIleLysAsnHisLysAsnLeuSerPheArgValSerSerAsn
TTCCAGTACCAGCTAGTGATAAAAATCATAAACAATTAAGCTTTCGAGTATCTTCTAAT        920

LysLeuSerGluLysAlaPheSerIleSerGlnLeuGlnLysAsnHisAspMetAsnAsp
AAATTATCAGAGAAAGCATTTAGCATCAGTCAGTTGCAAAAAAATCATGACATGAATGAT      980

GluLeuHisLeuCysTyrGlnPheLeuGlnGlyLysSerLeuAspIleLeuLeuGluSer
GAGCTTCACCTCTGCTATCAATTTTTGCAAGGCAAATCTTTGGACATACTCTTGGAAAGC     1040
                                                           exon 3
MetMetGlnAsnLeuLysGlnValPheGluProGlnLeuLeuLysThrThrSerTrpAsp
ATGATGCAGAATCTAAAACAAGTTTTTGAACCCCAGCTGTTAAAAACCACAAGTTGGGAC     1100

ThrAlaGluLeuTyrProPheCysSerSerIleIlePheGluIleThrPheThrThrIle
ACGGCAGAACTGTATCCATTCTGCAGCTCAATAATATTTGAGATCACATTTACAACTATA     1160

TyrGlyLysValIleValCysAspAsnAsnLysPheIleSerGluLeuArgAspAspPhe
TATGGAAAAGTTATTGTTTGTGACAACAACAAATTTATTAGTGAGCTAAGAGATGATTTT     1220

LeuLysPheAspAspLysPheAlaTyrLeuValSerAsnIleProIleGluLeuLeyGly
TTAAAATTTGATGACAAGTTTGCATATTTAGTATCCAACATACCCATTGAGCTTCTAGGA     1280

AsnValLysSerIleArgGluKysIleIleLysCysPheSerSerGluLysLeuAlaLys
AATGTCAAGTCTATTAGAGAGAAAATTATAAAATGCTTCTCATCAGAAAAGTTAGCCAAG     1340

MetGlnGlyTrpSerGluValPheGlnSerArgGlnAspAspLeuGluLysTyrTyrVal
ATGCAAGGATGGTCAGAAGTTTTTCAAAGCAGGCAAGATGACCTGGAGAAATATTATGTG     1400

HisGluAspLeuGluIleGlyA-
CACGAGGACCTTGAAATAGGAGgtaagaacttctgaatgagcacttgcctaaataaaaat     1460 catttacatagacctctgaaataaaaaagacaaaatggcgaccttgaaaatttttttat      1520 gctctttctaattggctaatgataaatgtttactctgatataacctctataattgatatt    1580 ttttttttttgctgaggtggtaaacagatacttaatggtgataatgagaaagcgtataact   1640
                                                         intron 3
aagctgcatttatccctcttatctcatccccgaccacaccgccccccccatacacattac    1700 attttaaactattctcattaagcagaaaattagacttcagaagcctattggttctcatta   1760 gcatgcagtgatccttggctggtctgtgtcctaacatcttttaattagcacactgcaaat   1820
                                                      -laHisHis
ctaatcagtgtaataaacgctattaatcttccttacacttattttctcccaCACATCAT    1880

PheGlyPheLeuTrpValSerValAlaSerThrIleProThrMetPheTrpAlaThrTyr
TTAGGCTTTCTCTGGGCCTCTGTGGCAAACACTATTCCAACTATGTTCTGGGCAACGTAT    1940
                                                           exon 4
TyrLeuLeuArgHisProGluAlaMetAlaAlaValArgAspGluIleAspArgLeuLeu
TATCTTCTGCGGCACCCAGAAGCTATGGCAGCAGTGCGTGACGAAATTGACCGTTTGCTG   2000

GlnSerThrGlyGlnLysGluGlySerGlyPheProIleHisLeuThrArgGluGlnLeu
CAGTCAACAGGTCAAAAGGAAGGGTCTGGATTTCCCATCCACCTCACCAGAGAACAATTG   2060

AspSerLeuIleCysLeu
GACAGCCTAATCTGCCTAGgtaattattttatctgttatgaagaagaaggtacctctct   2120 gcaaactcggtttatcactcatagctgtttacaagaggtagaggacacagctgctaattg  2180 acataataactcccatttacatcaattataaattatgtagtttatagccgtagatcatct  2240
                                                         intron 4
cattgcatgtaaacataaggcctaxgtaattaactgtgxaaxgtatgxaaaaxxctaacc   2300 aaagctt(--550nt-)cctgactgaacttcttactgccaaagttaaattccataccaat  2960 gagttattctctattctctctgtattgacatttcatctgcggtatcctttagggtacaat   3020 attccaagtttcttagacaaacgcaggaacaaatgttcacatatttctgtttctttatt    3080 cctttgacaagtaggcgagcattttagcctatgttggtctcaaaaaaatctttaaata     3140 tgttccaggttcttaatgggacctttcaggagcaaaagtcctcccaggtttggtcaatg   3200 ttcaccctcxgtggccattgaggaaaatgcccxxxxxgttctagagattgttctcacttc  3260
```

-continued

```
tcaggctaaggcccattgagcaatgccagaaagcatgccttatactagcagtcaatttgg    3320 aagtttgtagtttgtgtctttagcataggttatcaaataaattttatatttxcttttaaa    3380 aaaatctcaacattactaaaatacaaatatccttttattttctttgcagaattatcggg     3440 gaacaaatccagaaaatttgtgtaaatttcgggtagttgctccacttgatacacagtatt    3500 tctgcatattgtaatttctatgaagatctaggttgcatttcccatacattcaagcagttt    3560 ccattgcatttttatgaataagatgacgcatactgggaagtaaggcaaatacactaaaag    3620 gaatatgtgtttgtattctgtatagttattactcttaaaaaaagtagttgtaattcatcc    3680 actctttttactttcaactttttgctattaaaaaatcattttaaatttcagtattaaag    3740 cagaaacatttaaatttattagaccagaaaaataacagattctagaactataatttgaat    3800 ccatttaagcccatagctagagctagagattttcactattggatcc    3846
```

---

What is claimed is:

1. A isolated cytochrome P450 protein, at least a portion of which is encoded by a DNA molecule selected from the following:
   (a) DNA molecules containing the coding sequence set forth in SEQ ID NO:1 beginning at nucleotide 1 and ending at nucleotide 1242,
   (b) DNA molecules containing the coding sequence set forth in SEQ ID NO:3 beginning at nucleotide 81 and ending at nucleotide 1601,
   (c) DNA molecules comprising a Cyp7b protein coding sequence and which are capable of hybridizing with the DNA molecule defined in (a) or (b) under standard hybridization conditions defined as 2×SSC at 65° C.
   (d) Cytochrome P450-encoding DNA molecules capable of hybridizing with the DNA molecule defined in (a), (b) or (c) under reduced stringency conditions defined as 6×SSC at 65° C.

2. A cytochrome P450 protein according to claim 1(c) or (d) molecule comprising a Cyp7b gene associated sequence of another vertebrate sequence, especially a mammalian species and in particular a human Cyp7b gene-associated sequence.

3. A cytochrome P450 protein according to claim 2, at least a portion of which is encoded by a DNA molecule selected from the following:
   (e) DNA molecules comprising one or more sequences selected from
       (i) the sequence from position 831 to 1422 in SEQ ID NO:5, and
       (ii) the sequence from position 1873 to 2078 in SEQ ID NO:5,
   (f) DNA molecules comprising a Cyp7b gene exon which is capable of hybridizing with the DNA molecules defined in (e) under standard hybridization conditions defined as 2X SSC at 65° C.,
   (g) cytochrome P450-encoding DNA molecules capable of hybridizing with the DNA molecules defined in (e) or (f) under reduced stringency hybridization conditions defined as 6X SSC at 55° C.

4. A cytochrome P450 protein according to claim 2, at least a portion of which is encoded by a DNA molecule comprising a human Cyp7b gene associated sequence selected from the following:
   (e) DNA molecules comprising one or more sequences selected from (i) the sequence from position 831 to 1422 in SEQ ID NO:5, and (ii) the sequence from position 1873 to 2078 in SEQ ID NO:5, (f) DNA molecules comprising a Cyp7b gene exon which is capable of hybridizing with the DNA molecules defined in (e) under standard hybridization conditions defined as 2X SSC at 65° C., (g) cytochrome P450-encoding DNA molecules capable of hybridizing with the DNA molecules defined in (e) or (f) under reduced stringency hybridization conditions defined as 6X SSC at 55° C.

5. A cytochrome P450 protein according to claim 2, at least a portion of which is encoded by a DNA molecule comprising a human Cyp7b gene associated sequence selected from the following:

(h) DNA molecules comprising one or more contiguous pairs of sequences selected from
(i) the sequence from position 831 to 1422 in SEQ ID NO:5, and
(ii) the sequence from position 1873 to 2078 in SEQ ID NO:5, (i) DNA molecules comprising a Cyp7b gene exon which is capable of hybridizing with the DNA molecules defined in (e) under standard hybridization conditions defined as 2X SSC at 65° C., (j) cytochrome P450-encoding DNA molecules capable of hybridizing with the DNA molecules defined in (e) or (f) under reduced stringency hybridization conditions defined as 6X SSC at 55° C.

6. A cytochrome P450 protein according to claim 2, at least a portion of which is encoded by a DNA molecule comprising a human Cyp7b gene associated coding sequence selected from the following:

(k) DNA molecules comprising a contiguous coding sequence consisting of sequences from positions 831–1422 and 1873–2078 in SEQ ID NO:5. and (l) DNA molecules comprising Cyp7b gene exon coding sequences which are capable of hybridizing with the DNA molecules as defined in (k) under standard hybridization conditions defined as 2X SSC at 65° C., (m) cytochrome P450-encoding DNA molecules capable of hybridizing with the DNA molecules defined in (k) or (l) under reduced stringency hybridization conditions defined as 6X SSC at 55° C.

7. A cytochrome P450 protein, at least a portion of which is encoded by a DNA molecule encoding a Cyp7b gene associated coding sequence coded for by a DNA molecule as claimed in claim 1, but which differs in sequence from the sequences of the DNA molecules claimed in claims 1, 2, 3, 4, 5, and 6 by virtue of one or more amino acids of said Cyp7b gene-associated sequences being encoded by degenerate codons.

8. An isolated protein selected from the following:

(i) the protein designated rat Cyp7b comprising the amino acid sequence set forth in SEQ ID NO:2, (ii) the protein designated mouse Cyp7b comprising the amino acid sequence set forth in SEQ ID NO:4, and (ii) the protein designated as human Cyp7b comprising the amino acid sequence set forth in SEQ ID NO: 6.

* * * * *

SEQUENCE LISTING (1) GENERAL INFORMATION:

(iii) NUMBER OF SEQUENCES: 45

(2) INFORMATION FOR SEQ ID NO: 1:

(i) SEQUENCE CHARACTERISTICS:
      (A) LENGTH: 1763 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: rat (ix) FEATURE:
      (A) NAME/KEY: CDS
      (B) LOCATION: 1..1242

(xi) SEQUENCE DESCRIPTION: SEQ ID NO: 1:

```
GCC TTG GAG TAC CAG TAT GTA ATG AAA AAC CCA AAA CAA TTA AGC TTT        48
Ala Leu Glu Tyr Gln Tyr Val Met Lys Asn Pro Lys Gln Leu Ser Phe
 1               5                  10                  15

GAG AAG TTC AGC CGA AGA TTA TCA GCG AAA GCC TTC TCT GTC AAG AAG        96
Glu Lys Phe Ser Arg Arg Leu Ser Ala Lys Ala Phe Ser Val Lys Lys
            20                  25                  30

CTG CTA ACT AAT GAC GAC CTT AGC AAT GAC ATT CAC AGA GGC TAT CTT       144
Leu Leu Thr Asn Asp Asp Leu Ser Asn Asp Ile His Arg Gly Tyr Leu
        35                  40                  45

CTT TTA CAA GGC AAA TCT CTG GAT GGT CTT CTG GAA ACC ATG ATC CAA       192
Leu Leu Gln Gly Lys Ser Leu Asp Gly Leu Leu Glu Thr Met Ile Gln
    50                  55                  60

GAA GTA AAA GAA ATA TTT GAG TCC AGA CTG CTA AAA CTC ACA GAT TGG       240
Glu Val Lys Glu Ile Phe Glu Ser Arg Leu Leu Lys Leu Thr Asp Trp
65                  70                  75                  80

AAT ACA GCA AGA GTA TTT GAT TTC TGT AGT TCA CTG GTA TTT GAA ATC       288
Asn Thr Ala Arg Val Phe Asp Phe Cys Ser Ser Leu Val Phe Glu Ile
                85                  90                  95

ACA TTT ACA ACT ATA TAT GGA AAA ATT CTT GCT GCT AAC AAA AAA CAA       336
Thr Phe Thr Thr Ile Tyr Gly Lys Ile Leu Ala Ala Asn Lys Lys Gln
            100                 105                 110

ATT ATC AGT GAG CTG AGG GAT GAT TTT TTA AAA TTT GAT GAC CAT TTC       384
```

```
Ile Ile Ser Glu Leu Arg Asp Asp Phe Leu Lys Phe Asp Asp His Phe
            115                 120                 125

CCA TAC TTA GTA TCT GAC ATA CCT ATT CAG CTT CTA AGA AAT GCA GAA        432
Pro Tyr Leu Val Ser Asp Ile Pro Ile Gln Leu Leu Arg Asn Ala Glu
        130                 135                 140

TTT ATG CAG AAG AAA ATT ATA AAA TGT CTC ACA CCA GAA AAA GTA GCT        480
Phe Met Gln Lys Lys Ile Ile Lys Cys Leu Thr Pro Glu Lys Val Ala
145                 150                 155                 160

CAG ATG CAA AGA CGG TCA GAA ATT GTT CAG GAG AGG CAG GAG ATG CTG        528
Gln Met Gln Arg Arg Ser Glu Ile Val Gln Glu Arg Gln Glu Met Leu
                165                 170                 175

AAA AAA TAC TAC GGG CAT GAA GAG TTT GAA ATA GGA GCA CAT CAT CTT        576
Lys Lys Tyr Tyr Gly His Glu Glu Phe Glu Ile Gly Ala His His Leu
            180                 185                 190

GGC TTG CTC TGG GCC TCT CTA GCA AAC ACC ATT CCA GCT ATG TTC TGG        624
Gly Leu Leu Trp Ala Ser Leu Ala Asn Thr Ile Pro Ala Met Phe Trp
        195                 200                 205

GCA ATG TAT TAT CTT CTT CAG CAT CCA GAA GCT ATG GAA GTC CTG CGT        672
Ala Met Tyr Tyr Leu Leu Gln His Pro Glu Ala Met Glu Val Leu Arg
210                 215                 220

GAC GAA ATT GAC AGC TTC CTG CAG TCA ACA GGT CAA AAG AAA GGA CCT        720
Asp Glu Ile Asp Ser Phe Leu Gln Ser Thr Gly Gln Lys Lys Gly Pro
225                 230                 235                 240

GGA ATT TCT GTC CAC TTC ACC AGA GAA CAA TTG GAC AGC TTG GTC TGC        768
Gly Ile Ser Val His Phe Thr Arg Glu Gln Leu Asp Ser Leu Val Cys
                245                 250                 255

CTG GAA AGC GCT ATT CTT GAG GTT CTG AGG TTG TGC TCC TAC TCC AGC        816
Leu Glu Ser Ala Ile Leu Glu Val Leu Arg Leu Cys Ser Tyr Ser Ser
            260                 265                 270

ATC ATC CGT GAA GTG CAA GAG GAT ATG GAT TTC AGC TCA GAG AGT AGG        864
Ile Ile Arg Glu Val Gln Glu Asp Met Asp Phe Ser Ser Glu Ser Arg
        275                 280                 285

AGC TAC CGT CTG CGG AAA GGA GAC TTT GTA GCT GTC TTT CCT CCA ATG        912
Ser Tyr Arg Leu Arg Lys Gly Asp Phe Val Ala Val Phe Pro Pro Met
        290                 295                 300

ATA CAC AAT GAC CCA GAA GTC TTC GAT GCT CCA AAG GAC TTT AGG TTT        960
Ile His Asn Asp Pro Glu Val Phe Asp Ala Pro Lys Asp Phe Arg Phe
305                 310                 315                 320

GAT CGC TTC GTA GAA GAT GGT AAG AAG AAA ACA ACG TTT TTC AAA GGA       1008
Asp Arg Phe Val Glu Asp Gly Lys Lys Lys Thr Thr Phe Phe Lys Gly
                325                 330                 335

GGA AAA AAG CTG AAG AGT TAC ATT ATA CCA TTT GGA CTT GGA ACA AGC       1056
Gly Lys Lys Leu Lys Ser Tyr Ile Ile Pro Phe Gly Leu Gly Thr Ser
            340                 345                 350

AAA TGT CCA GGC AGA TAC TTT GCA ATT AAT GAA ATG AAG CTA CTA GTG       1104
Lys Cys Pro Gly Arg Tyr Phe Ala Ile Asn Glu Met Lys Leu Leu Val
        355                 360                 365

ATT ATA CTT TTA ACT TAT TTT GAT TTA GAA GTC ATT GAC ACT AAG CCT       1152
Ile Ile Leu Leu Thr Tyr Phe Asp Leu Glu Val Ile Asp Thr Lys Pro
370                 375                 380

ATA GGA CTA AAC CAC AGT CGC ATG TTT CTG GGC ATT CAG CAT CCA GAC       1200
Ile Gly Leu Asn His Ser Arg Met Phe Leu Gly Ile Gln His Pro Asp
385                 390                 395                 400

TCT GAC ATC TCA TTT AGG TAC AAG GCA AAA TCT TGG AGA TCC               1242
Ser Asp Ile Ser Phe Arg Tyr Lys Ala Lys Ser Trp Arg Ser
                405                 410

TGAAAGGGTG GCAGAGAAGC TTAGCGGAAT AAGGCTGCAC ATGCTGAGCT CTGTGATT      1302

CTGTACTCCC CAAATGCAGC CACTATTCTT GTTTGTTAGA AAATGGCAAA TTTTTATT      1362
```

-continued

```
ATTGCGATCC ATCCAGTTTG TTTTGGGTCA CAAAACCTGT CATAAAATAA AGCGCTGT      1422

TGGTGTAAAA AAATGTCATG GCAATCATTT CAGGATAAGG TAAAATAACG TTTTCAAG      1482

TGTACTTACT ATGATTTTTA TCATTTGTAG TGAATGTGCT TTTCCAGTAA TAAATTTG      1542

CCAGGGTGAT TTTTTTTAAT TACTGAAATC CTCTAATATC GGTTTTATGT GCTGCCAG      1602

AACTCTGCCA TCAATGGACA GTATAACAAT TTCCAGTTTT CCAGAGAAGG GAGAAATT      1662

GCCCCATGAG TTACGCTGTA TAAAATTGTT CTCTTCAACT ATAATATCAA TAATGTCT      1722

ATCACCAGGT TACCTTTGCA TTAAATCGAG TTTTGCAAAA G                        1763
```

(2) INFORMATION FOR SEQ ID NO: 2:

(i) SEQUENCE CHARACTERISTICS:
        (A) LENGTH: 414 amino acids
        (B) TYPE: amino acid
        (D) TOPOLOGY: linear (ii) MOLECULE TYPE: protein (xi) SEQUENCE DESCRIPTION: SEQ ID NO: 2:

```
Ala Leu Glu Tyr Gln Tyr Val Met Lys Asn Pro Lys Gln Leu Ser Phe
 1               5                  10                  15

Glu Lys Phe Ser Arg Arg Leu Ser Ala Lys Ala Phe Ser Val Lys Lys
                20                  25                  30

Leu Leu Thr Asn Asp Asp Leu Ser Asn Asp Ile His Arg Gly Tyr Leu
            35                  40                  45

Leu Leu Gln Gly Lys Ser Leu Asp Gly Leu Leu Glu Thr Met Ile Gln
        50                  55                  60

Glu Val Lys Glu Ile Phe Glu Ser Arg Leu Leu Lys Leu Thr Asp Trp
65                  70                  75                  80

Asn Thr Ala Arg Val Phe Asp Phe Cys Ser Ser Leu Val Phe Glu Ile
                85                  90                  95

Thr Phe Thr Thr Ile Tyr Gly Lys Ile Leu Ala Ala Asn Lys Lys Gln
                100                 105                 110

Ile Ile Ser Glu Leu Arg Asp Asp Phe Leu Lys Phe Asp His Phe
            115                 120                 125

Pro Tyr Leu Val Ser Asp Ile Pro Ile Gln Leu Leu Arg Asn Ala Glu
        130                 135                 140

Phe Met Gln Lys Lys Ile Ile Lys Cys Leu Thr Pro Glu Lys Val Ala
145                 150                 155                 160

Gln Met Gln Arg Arg Ser Glu Ile Val Gln Glu Arg Gln Glu Met Leu
                165                 170                 175

Lys Lys Tyr Tyr Gly His Glu Glu Phe Glu Ile Gly Ala His His Leu
                180                 185                 190

Gly Leu Leu Trp Ala Ser Leu Ala Asn Thr Ile Pro Ala Met Phe Trp
            195                 200                 205

Ala Met Tyr Tyr Leu Leu Gln His Pro Glu Ala Met Glu Val Leu Arg
        210                 215                 220

Asp Glu Ile Asp Ser Phe Leu Gln Ser Thr Gly Gln Lys Lys Gly Pro
225                 230                 235                 240

Gly Ile Ser Val His Phe Thr Arg Glu Gln Leu Asp Ser Leu Val Cys
                245                 250                 255

Leu Glu Ser Ala Ile Leu Glu Val Leu Arg Leu Cys Ser Tyr Ser Ser
                260                 265                 270

Ile Ile Arg Glu Val Gln Glu Asp Met Asp Phe Ser Ser Glu Ser Arg
            275                 280                 285
```

```
Ser Tyr Arg Leu Arg Lys Gly Asp Phe Val Ala Val Phe Pro Pro Met
    290                 295                 300

Ile His Asn Asp Pro Glu Val Phe Asp Ala Pro Lys Asp Phe Arg Phe
305                 310                 315                 320

Asp Arg Phe Val Glu Asp Gly Lys Lys Thr Thr Phe Phe Lys Gly
                325                 330                 335

Gly Lys Lys Leu Lys Ser Tyr Ile Ile Pro Phe Gly Leu Gly Thr Ser
                340                 345                 350

Lys Cys Pro Gly Arg Tyr Phe Ala Ile Asn Glu Met Lys Leu Leu Val
            355                 360                 365

Ile Ile Leu Leu Thr Tyr Phe Asp Leu Glu Val Ile Asp Thr Lys Pro
370                 375                 380

Ile Gly Leu Asn His Ser Arg Met Phe Leu Gly Ile Gln His Pro Asp
385                 390                 395                 400

Ser Asp Ile Ser Phe Arg Tyr Lys Ala Lys Ser Trp Arg Ser
                405                 410

(2) INFORMATION FOR SEQ ID NO: 3:

(i) SEQUENCE CHARACTERISTICS:
        (A) LENGTH: 1880 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: mouse (ix) FEATURE:
        (A) NAME/KEY: CDS
        (B) LOCATION: 81..1601

(xi) SEQUENCE DESCRIPTION: SEQ ID NO: 3:

GGCAGGCACA GCCTCTGGTC TAAGAAGAGA GGGCACTGTG CAAAAGCCAT CGCTCCCTAC        60

AGAGCCGCCA GCTCGTCGGG ATG CAG GGA GCC ACG ACC CTA GAT GCC GCC          110
               Met Gln Gly Ala Thr Thr Leu Asp Ala Ala
                 1               5                  10

TCG CCA GGG CCT CTC GCC CTC CTA GGC CTT CTC TTT GCC GCC ACC TTA        158
Ser Pro Gly Pro Leu Ala Leu Leu Gly Leu Leu Phe Ala Ala Thr Leu
            15                  20                  25

CTG CTC TCG GCC CTG TTC CTC CTC ACC CGG CGC ACC AGG CGC CCT CGT        206
Leu Leu Ser Ala Leu Phe Leu Leu Thr Arg Arg Thr Arg Arg Pro Arg
                30                  35                  40

GAA CCA CCC TTG ATA AAA GGT TGG CTT CCT TAT CTT GGC ATG GCC CTG        254
Glu Pro Pro Leu Ile Lys Gly Trp Leu Pro Tyr Leu Gly Met Ala Leu
            45                  50                  55

AAA TTC TTT AAG GAT CCG TTA ACT TTC TTG AAA ACT CTT CAA AGG CAA        302
Lys Phe Phe Lys Asp Pro Leu Thr Phe Leu Lys Thr Leu Gln Arg Gln
    60                  65                  70

CAT GGT GAC ACT TTC ACT GTC TTC CTT GTG GGG AAG TAT ATA ACA TTT        350
His Gly Asp Thr Phe Thr Val Phe Leu Val Gly Lys Tyr Ile Thr Phe
75                  80                  85                  90

GTT CTG AAC CCT TTC CAG TAC CAG TAT GTA ACG AAA AAC CCA AAA CAA        398
Val Leu Asn Pro Phe Gln Tyr Gln Tyr Val Thr Lys Asn Pro Lys Gln
                95                 100                 105

TTA AGC TTT CAG AAG TTC AGC AGC CGA TTA TCA GCG AAA GCC TTC TCT        446
Leu Ser Phe Gln Lys Phe Ser Ser Arg Leu Ser Ala Lys Ala Phe Ser
            110                 115                 120
```

-continued

| | |
|---|---|
| GTA AAG AAG CTG CTT ACT GAT GAC GAC CTT AAT GAA GAC GTT CAC AGA<br>Val Lys Lys Leu Leu Thr Asp Asp Asp Leu Asn Glu Asp Val His Arg<br>     125                        130                      135 | 494 |
| GCC TAT CTA CTT CTA CAA GGC AAA CCT TTG GAT GCT CTT CTG GAA ACT<br>Ala Tyr Leu Leu Leu Gln Gly Lys Pro Leu Asp Ala Leu Leu Glu Thr<br>     140                        145                      150 | 542 |
| ATG ATC CAA GAA GTA AAA GAA TTA TTT GAG TCC CAA CTG CTA AAA ATC<br>Met Ile Gln Glu Val Lys Glu Leu Phe Glu Ser Gln Leu Leu Lys Ile<br>155                     160                      165                     170 | 590 |
| ACA GAT TGG AAC ACA GAA AGA ATA TTT GCA TTC TGT GGC TCA CTG GTA<br>Thr Asp Trp Asn Thr Glu Arg Ile Phe Ala Phe Cys Gly Ser Leu Val<br>                 175                      180                     185 | 638 |
| TTT GAG ATC ACA TTT GCG ACT CTA TAT GGA AAA ATT CTT GCT GGT AAC<br>Phe Glu Ile Thr Phe Ala Thr Leu Tyr Gly Lys Ile Leu Ala Gly Asn<br>                 190                      195                     200 | 686 |
| AAG AAA CAA ATT ATC AGT GAG CTA AGG GAT GAT TTT TTT AAA TTT GAT<br>Lys Lys Gln Ile Ile Ser Glu Leu Arg Asp Asp Phe Phe Lys Phe Asp<br>                 205                      210                     215 | 734 |
| GAC ATG TTC CCA TAC TTA GTA TCT GAC ATA CCT ATT CAG CTT CTA AGA<br>Asp Met Phe Pro Tyr Leu Val Ser Asp Ile Pro Ile Gln Leu Leu Arg<br>220                     225                      230 | 782 |
| AAT GAA GAA TCT ATG CAG AAG AAA ATT ATA AAA TGC CTC ACA TCA GAA<br>Asn Glu Glu Ser Met Gln Lys Lys Ile Ile Lys Cys Leu Thr Ser Glu<br>235                     240                      245                     250 | 830 |
| AAA GTA GCT CAG ATG CAA GGA CAG TCA AAA ATT GTT CAG GAA AGC CAA<br>Lys Val Ala Gln Met Gln Gly Gln Ser Lys Ile Val Gln Glu Ser Gln<br>                 255                      260                     265 | 878 |
| GAT CTG CTG AAA AGA TAC TAT AGG CAT GAC GAT TCT GAA ATA GGA GCA<br>Asp Leu Leu Lys Arg Tyr Tyr Arg His Asp Asp Ser Glu Ile Gly Ala<br>                 270                      275                     280 | 926 |
| CAT CAT CTT GGC TTT CTC TGG GCC TCT CTA GCA AAC ACC ATT CCA GCT<br>His His Leu Gly Phe Leu Trp Ala Ser Leu Ala Asn Thr Ile Pro Ala<br>                 285                      290                     295 | 974 |
| ATG TTC TGG GCA ATG TAT TAT ATT CTT CGG CAT CCT GAA GCT ATG GAA<br>Met Phe Trp Ala Met Tyr Tyr Ile Leu Arg His Pro Glu Ala Met Glu<br>300                     305                      310 | 1022 |
| GCC CTG CGT GAC GAA ATT GAC AGT TTC CTG CAG TCA ACA GGT CAA AAG<br>Ala Leu Arg Asp Glu Ile Asp Ser Phe Leu Gln Ser Thr Gly Gln Lys<br>315                     320                      325                     330 | 1070 |
| AAA GGG CCT GGA ATT TCA GTC CAC TTC ACC AGA GAA CAA TTG GAC AGC<br>Lys Gly Pro Gly Ile Ser Val His Phe Thr Arg Glu Gln Leu Asp Ser<br>                 335                      340                     345 | 1118 |
| TTG GTC TGC CTG GAA AGC ACT ATT CTT GAG GTT CTG AGG CTG TGC TCA<br>Leu Val Cys Leu Glu Ser Thr Ile Leu Glu Val Leu Arg Leu Cys Ser<br>                 350                      355                     360 | 1166 |
| TAC TCC AGC ATC ATC CGA GAA GTG CAG GAG GAT ATG AAT CTC AGC TTA<br>Tyr Ser Ser Ile Ile Arg Glu Val Gln Glu Asp Met Asn Leu Ser Leu<br>                 365                      370                     375 | 1214 |
| GAG AGT AAG AGT TTC TCT CTG CGG AAA GGA GAT TTT GTA GCC CTC TTT<br>Glu Ser Lys Ser Phe Ser Leu Arg Lys Gly Asp Phe Val Ala Leu Phe<br>380                     385                      390 | 1262 |
| CCT CCA CTC ATA CAC AAT GAC CCG GAA ATC TTC GAT GCT CCA AAG GAA<br>Pro Pro Leu Ile His Asn Asp Pro Glu Ile Phe Asp Ala Pro Lys Glu<br>395                     400                      405                     410 | 1310 |
| TTT AGG TTC GAT CGG TTC ATA GAA GAT GGT AAG AAG AAA AGC ACG TTT<br>Phe Arg Phe Asp Arg Phe Ile Glu Asp Gly Lys Lys Lys Ser Thr Phe<br>                 415                      420                     425 | 1358 |
| TTC AAA GGA GGG AAG AGG CTG AAG ACT TAC GTT ATG CCT TTT GGA CTC<br>Phe Lys Gly Gly Lys Arg Leu Lys Thr Tyr Val Met Pro Phe Gly Leu<br>                 430                      435                     440 | 1406 |

```
GGA ACA AGC AAA TGT CCA GGG AGA TAT TTT GCA GTG AAC GAA ATG AAG    1454
Gly Thr Ser Lys Cys Pro Gly Arg Tyr Phe Ala Val Asn Glu Met Lys
            445                 450                 455

CTA CTG CTG ATT GAG CTT TTA ACT TAT TTT GAT TTA GAA ATT ATC GAC    1502
Leu Leu Leu Ile Glu Leu Leu Thr Tyr Phe Asp Leu Glu Ile Ile Asp
        460                 465                 470

AGG AAG CCT ATA GGG CTA AAT CAC AGT CGG ATG TTT TTA GGT ATT CAG    1550
Arg Lys Pro Ile Gly Leu Asn His Ser Arg Met Phe Leu Gly Ile Gln
475                 480                 485                 490

CAC CCC GAT TCT GCC GTC TCC TTT AGG TAC AAA GCA AAA TCT TGG AGA    1598
His Pro Asp Ser Ala Val Ser Phe Arg Tyr Lys Ala Lys Ser Trp Arg
                495                 500                 505

AGC TGAAAGTGTG GCAGAGAAGC TTTGCAGAGT AAGGCTGCAT GTGCTGAGCT         1651
Ser

CCGTGATTTG GTGCACTCCC CCAAATGCAA CCGCTACTCT TGTTTGAAAA TGGCAAAT    1711

ATATTTGGTT GAGATCAATC CAGTTGGTTT TGGGTCACAA AACCTGTCAT AAAATAAA    1771

AGTGTGATGG TTTAAAAAAT GTCATGGCAA TCATTTCAGG ATAAGGTAAA ATAACATT    1831

CAAGTTTGTA CTTACTATGA TTTTTATCAT TTGTAGTGAA TGTGCTTTT             1880
```

(2) INFORMATION FOR SEQ ID NO: 4:

(i) SEQUENCE CHARACTERISTICS:
        (A) LENGTH: 507 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Gln Gly Ala Thr Thr Leu Asp Ala Ala Ser Pro Gly Pro Leu Ala
 1               5                  10                  15

Leu Leu Gly Leu Leu Phe Ala Ala Thr Leu Leu Ser Ala Leu Phe
                20                  25                  30

Leu Leu Thr Arg Arg Thr Arg Arg Pro Arg Glu Pro Pro Leu Ile Lys
            35                  40                  45

Gly Trp Leu Pro Tyr Leu Gly Met Ala Leu Lys Phe Phe Lys Asp Pro
 50                  55                  60

Leu Thr Phe Leu Lys Thr Leu Gln Arg Gln His Gly Asp Thr Phe Thr
 65                  70                  75                  80

Val Phe Leu Val Gly Lys Tyr Ile Thr Phe Val Leu Asn Pro Phe Gln
                85                  90                  95

Tyr Gln Tyr Val Thr Lys Asn Pro Lys Gln Leu Ser Phe Gln Lys Phe
                100                 105                 110

Ser Ser Arg Leu Ser Ala Lys Ala Phe Ser Val Lys Lys Leu Leu Thr
            115                 120                 125

Asp Asp Asp Leu Asn Glu Asp Val His Arg Ala Tyr Leu Leu Leu Gln
130                 135                 140

Gly Lys Pro Leu Asp Ala Leu Leu Glu Thr Met Ile Gln Glu Val Lys
145                 150                 155                 160

Glu Leu Phe Glu Ser Gln Leu Leu Lys Ile Thr Asp Trp Asn Thr Glu
                165                 170                 175

Arg Ile Phe Ala Phe Cys Gly Ser Leu Val Phe Glu Ile Thr Phe Ala
            180                 185                 190

Thr Leu Tyr Gly Lys Ile Leu Ala Gly Asn Lys Lys Gln Ile Ile Ser
            195                 200                 205
```

```
Glu Leu Arg Asp Asp Phe Phe Lys Phe Asp Asp Met Phe Pro Tyr Leu
    210                 215                 220

Val Ser Asp Ile Pro Ile Gln Leu Leu Arg Asn Glu Glu Ser Met Gln
225                 230                 235                 240

Lys Lys Ile Ile Lys Cys Leu Thr Ser Glu Lys Val Ala Gln Met Gln
                245                 250                 255

Gly Gln Ser Lys Ile Val Gln Gly Ser Gln Asp Leu Leu Lys Arg Tyr
            260                 265                 270

Tyr Arg His Asp Asp Ser Glu Ile Gly Ala His His Leu Gly Phe Leu
        275                 280                 285

Trp Ala Ser Leu Ala Asn Thr Ile Pro Ala Met Phe Trp Ala Met Tyr
    290                 295                 300

Tyr Ile Leu Arg His Pro Glu Ala Met Glu Ala Leu Arg Asp Glu Ile
305                 310                 315                 320

Asp Ser Phe Leu Gln Ser Thr Gly Gln Lys Lys Gly Pro Gly Ile Ser
                325                 330                 335

Val His Phe Thr Arg Glu Gln Leu Asp Ser Leu Val Cys Leu Glu Ser
                340                 345                 350

Thr Ile Leu Glu Val Leu Arg Leu Cys Ser Tyr Ser Ser Ile Ile Arg
            355                 360                 365

Glu Val Gln Glu Asp Met Asn Leu Ser Leu Glu Ser Lys Ser Phe Ser
            370                 375                 380

Leu Arg Lys Gly Asp Phe Val Ala Leu Phe Pro Pro Leu Ile His Asn
385                 390                 395                 400

Asp Pro Glu Ile Phe Asp Ala Pro Lys Glu Phe Arg Phe Asp Arg Phe
                405                 410                 415

Ile Glu Asp Gly Lys Lys Ser Thr Phe Phe Lys Gly Gly Lys Arg
            420                 425                 430

Leu Lys Thr Tyr Val Met Pro Phe Gly Leu Gly Thr Ser Lys Cys Pro
        435                 440                 445

Gly Arg Tyr Phe Ala Val Asn Glu Met Lys Leu Leu Leu Ile Glu Leu
450                 455                 460

Leu Thr Tyr Phe Asp Leu Glu Ile Ile Asp Arg Lys Pro Ile Gly Leu
465                 470                 475                 480

Asn His Ser Arg Met Phe Leu Gly Ile Gln His Pro Asp Ser Ala Val
                485                 490                 495

Ser Phe Arg Tyr Lys Ala Lys Ser Trp Arg Ser
            500                 505

(2) INFORMATION FOR SEQ ID NO: 5:

(i) SEQUENCE CHARACTERISTICS:
        (A) LENGTH: 3846 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: human (ix) FEATURE:
        (A) NAME/KEY: CDS
        (B) LOCATION: join(831..1422, 1873..2078)

(ix) FEATURE:
        (A) NAME/KEY: intron
        (B) LOCATION: 1..830
```

(ix) FEATURE:
    (A) NAME/KEY: exon
    (B) LOCATION: 831..1422

(ix) FEATURE:
    (A) NAME/KEY: intron
    (B) LOCATION: 1423..1872

(ix) FEATURE:
    (A) NAME/KEY: exon
    (B) LOCATION: 1873..2078

(ix) FEATURE:
    (A) NAME/KEY: intron
    (B) LOCATION: 2079..3846

(xi) SEQUENCE DESCRIPTION: SEQ ID NO: 5:

```
GGATCCAACC AAGTTTCCAG ATCTTATAAA TGTGGTGAAT GGTGAATGAC TTCCTGAAGA         60

ATGGATGAAT GGATGTGTTC TAGTTTGGAA TCCTGTGTCA GTCACAAGTC AATATGTGA         120

CTTGAACATG TTATTAAATC TCCCACATCC ATAAAAGTGA AAATGCTGGC ATTAGTGGA         180

TTTTGCCAGT GTTGAATTAG ACATTTATTT GTGAGTACCT GCTCCATACA GTATGGTCA         240

TTATTTGAGT TAAAATTGTT GTATTTGAAC AAAACTCAGA TGACACCTAA GCATGAAAA         300

GCTCTTTATG AAGTATAAAT ACTCAGAAAT GGAATGGCAT GTTGCCAATT TGTTTTCTG         360

TTTATTGAGG GAAATATATG AGAAGTATTT AAGTCAGGGG ATTATGAGGA ATATTTAAA         420

GATANNNNNN NNNNNNNNNN NNNNNNNNNN NNNNNNNNNN NNNNNNNNNN NNNNNNNN         480

NNNNNNNNNN NNNNNNNNNN NNNNNNNNNN NNNNNNNNNN NNNNNNNNNN NNNNNNNN         540

NNNNNNNNNN NNNNNNNNNN NNNNNNNNNN NNNNNNNNNN NNNNNNNNNN NNNNNNNN         600

NNNNNNNNNN NNNNNNNNNN NNNNNNNNNN NNNNTCTAGA GTGTTTTCCA CCATCTTTC         660

AAGGAAACAT GTAGTGTACC TTCGAATGAA ATGGATTTGT ATTAAACTTT TGCCTTAG         720

TATTAGGGTC TTTCTAATTT TGATTAACA TATTTTTTTA ATTTGTGGTG TTTATTTCT          780

TTTTTATTAA CAAACGAACT CATATGCTCC TCTCTCTTTT TTTTTTTCT GGA AAG           836
                                                         Gly Lys
                                                           1

TAC ATA ACA TTT ATA CCT GGA CCC TTC CAG TAC CAG CTA GTG ATA AAA         884
Tyr Ile Thr Phe Ile Pro Gly Pro Phe Gln Tyr Gln Leu Val Ile Lys
       5                  10                 15

AAT CAT AAA CAA TTA AGC TTT CGA GTA TCT TCT AAT AAA TTA TCA GAG         932
Asn His Lys Gln Leu Ser Phe Arg Val Ser Ser Asn Lys Leu Ser Glu
 20                  25                  30

AAA GCA TTT AGC ATC AGT CAG TTG CAA AAA AAT CAT GAC ATG AAT GAT         980
Lys Ala Phe Ser Ile Ser Gln Leu Gln Lys Asn His Asp Met Asn Asp
 35                  40                  45                  50

GAG CTT CAC CTC TGC TAT CAA TTT TTG CAA GGC AAA TCT TTG GAC ATA        1028
Glu Leu His Leu Cys Tyr Gln Phe Leu Gln Gly Lys Ser Leu Asp Ile
             55                  60                  65

CTC TTG GAA AGC ATG ATG CAG AAT CTA AAA CAA GTT TTT GAA CCC CAG        1076
Leu Leu Glu Ser Met Met Gln Asn Leu Lys Gln Val Phe Glu Pro Gln
         70                  75                  80

CTG TTA AAA ACC ACA AGT TGG GAC ACG GCA GAA CTG TAT CCA TTC TGC        1124
Leu Leu Lys Thr Thr Ser Trp Asp Thr Ala Glu Leu Tyr Pro Phe Cys
     85                  90                  95

AGC TCA ATA ATA TTT GAG ATC ACA TTT ACA ACT ATA TAT GGA AAA GTT        1172
Ser Ser Ile Ile Phe Glu Ile Thr Phe Thr Thr Ile Tyr Gly Lys Val
100                 105                 110

ATT GTT TGT GAC AAC AAC AAA TTT ATT AGT GAG CTA AGA GAT GAT TTT        1220
Ile Val Cys Asp Asn Asn Lys Phe Ile Ser Glu Leu Arg Asp Asp Phe
115                 120                 125                 130
```

```
TTA AAA TTT GAT GAC AAG TTT GCA TAT TTA GTA TCC AAC ATA CCC ATT        1268
Leu Lys Phe Asp Asp Lys Phe Ala Tyr Leu Val Ser Asn Ile Pro Ile
            135                 140                 145

GAG CTT CTA GGA AAT GTC AAG TCT ATT AGA GAG AAA ATT ATA AAA TGC        1316
Glu Leu Leu Gly Asn Val Lys Ser Ile Arg Glu Lys Ile Ile Lys Cys
            150                 155                 160

TTC TCA TCA GAA AAG TTA GCC AAG ATG CAA GGA TGG TCA GAA GTT TTT        1364
Phe Ser Ser Glu Lys Leu Ala Lys Met Gln Gly Trp Ser Glu Val Phe
            165                 170                 175

CAA AGC AGG CAA GAT GAC CTG GAG AAA TAT TAT GTG CAC GAG GAC CTT        1412
Gln Ser Arg Gln Asp Asp Leu Glu Lys Tyr Tyr Val His Glu Asp Leu
        180                 185                 190

GAA ATA GGA G GTAAGAACTT CTGAATGAGC ACTTGCCTAA ATAAAAATCA              1462
Glu Ile Gly
195

TTTACATAGA CCTCTGAAAT AAAAAAAGAC AAAATGGCGA CCTTGAAAAT TTTTTTAT        1522

TCTTTCTAAT TGGCTAATGA TAAATGTTTA CTCTGATATA ACCTCTATAA TTGATATT        1582

TTTTTTTGCT GAGGTGGTAA ACAGATACTT AATGGTGATA ATGAGAAAGC GTATAACT        1642

GCTGCATTTA TCCCTCTTAT CTCATCCCCG ACCACACCGC CCCCCCCATA CACATTAC        1702

TTTAAACTAT TCTCATTAAG CAGAAAATTA GACTTCAGAA GCCTATTGGT TCTCATTA        1762

ATGCAGTGAT CCTTGGCTGG TCTGTGTCCT AACATCTTTT AATTAGCACA CTGCAAAT        1822

AATCAGTGTA ATAAACGCTA TTAATCTTCC TTTACACTTA TTTTCTCCCA  CA CAT        1877
                                                         Ala His

CAT TTA GGC TTT CTC TGG GCC TCT GTG GCA AAC ACT ATT CCA ACT ATG        1925
His Leu Gly Phe Leu Trp Ala Ser Val Ala Asn Thr Ile Pro Thr Met
200                 205                 210                 215

TTC TGG GCA ACG TAT TAT CTT CTG CGG CAC CCA GAA GCT ATG GCA GCA        1973
Phe Trp Ala Thr Tyr Tyr Leu Leu Arg His Pro Glu Ala Met Ala Ala
            220                 225                 230

GTG CGT GAC GAA ATT GAC CGT TTG CTG CAG TCA ACA GGT CAA AAG GAA        2021
Val Arg Asp Glu Ile Asp Arg Leu Leu Gln Ser Thr Gly Gln Lys Glu
            235                 240                 245

GGG TCT GGA TTT CCC ATC CAC CTC ACC AGA GAA CAA TTG GAC AGC CTA        2069
Gly Ser Gly Phe Pro Ile His Leu Thr Arg Glu Gln Leu Asp Ser Leu
            250                 255                 260

ATC TGC CTA GGTAATTATT TTATCTGTTA TGAAGAAAGA AGGTACCTCT               2118
Ile Cys Leu
        265

CTGCAAACTC GGTTTATCAC TCATAGCTGT TTACAAGAGG TAGAGGACAC AGCTGCTA       2178

TGACATAATA ACTCCCATTT ACATCAATTA TAAATTATGT AGTTTATAGC CGTAGATC       2238

CTCATTGCAT GTAAACATAA GGCCTANGTA ATTAACTGTG NAANGTATGN AAAANNCT       2298

CCAAAGCTTN NNNNNNNNNN NNNNNNNNNN NNNNNNNNNN NNNNNNNNNN NNNNNNN        2358

NNNNNNNNNN NNNNNNNNNN NNNNNNNNNN NNNNNNNNNN NNNNNNNNNN NNNNNNN        2418

NNNNNNNNNN NNNNNNNNNN NNNNNNNNNN NNNNNNNNNN NNNNNNNNNN NNNNNNN        2478

NNNNNNNNNN NNNNNNNNNN NNNNNNNNNN NNNNNNNNNN NNNNNNNNNN NNNNNNN        2538

NNNNNNNNNN NNNNNNNNNN NNNNNNNNNN NNNNNNNNNN NNNNNNNNNN NNNNNNN        2598

NNNNNNNNNN NNNNNNNNNN NNNNNNNNNN NNNNNNNNNN NNNNNNNNNN NNNNNNN        2658

NNNNNNNNNN NNNNNNNNNN NNNNNNNNNN NNNNNNNNNN NNNNNNNNNN NNNNNNN        2718

NNNNNNNNNN NNNNNNNNNN NNNNNNNNNN NNNNNNNNNN NNNNNNNNNN NNNNNNN        2778

NNNNNNNNNN NNNNNNNNNN NNNNNNNNNN NNNNNNNNNN NNNNNNNNNN NNNNNNN        2838
```

```
NNNNNNNNNN NNNNNNNNNN NNNNNNNNNN NNNNNNNNNN NNNNNNNNNN NNNNNNNN         2898

NNNNNNNNNN NNNNNNNNNC CTGACTGAAC TTCTTACTGC CAAAGTTAAA TTCCATAC          2958

ATGAGTTATT CTCTATTCTC TCTGTATTGA CATTTCATCT GCGGTATCCT TTAGGGTA         3018

ATATTCCAAG TTTCTTTAGA CAAACGCAGG AACAAATGTT CACATATTTC TGTTTCTT         3078

TTCCTTTGAC AAGTAGGCGA GCATTTTAGC CTATGTTGGT CTCAAAAAAA ATCTTTTA         3138

TATGTTCCAG GTTCTTTAAT GGGACCTTTC AGGAGCAAAA GTCCTCCCAG GTTTGGTC         3198

TGTTCACCCT CNGTGGCCAT TGAGGAAAAT GCCCNNNNNG TTCTAGAGAT TGTTCTCA         3258

TCTCAGGCTA AGGCCCATTG AGCAATGCCA GAAAGCATGC CTTATACTAG CAGTCAAT         3318

GGAAGTTTGT AGTTTGTGTC TTTAGCATAG GTTATCAAAT AAATTTTATA TTTNCTTT         3378

AAAAAATCTC AACATTACTA AAATACAAAT ATCCTTTTAT TTTTCTTTGC AGAATTAT         3438

GGGAACAAAT CCAGAAAATT TGTGTAAATT TCGGGTAGTT GCTCCACTTG ATACACAG         3498

TTTCTGCATA TTGTAATTTC TATGAAGATC TAGGTTGCAT TTCCCATACA TTCAAGCA         3558

TTCCATTGCA TTTTTATGAA TAAGATGACG CATACTGGGA AGTAAGGCAA ATACACTA         3618

AGGAATATGT GTTTGTATTC TGTATAGTTA TTACTCTTAA AAAAGTAGT TGTAATTC          3678

CCACTCTTTT TACTTTCAAC TTTTTGCTAT TAAAAAATCA TTTTTAAATT TCAGTATT         3738

AGCAGAAACA TTTAAATTTA TTAGACCAGA AAAATAACAG ATTCTAGAAC TATAATTT         3798

ATCCATTTAA GCCCATAGCT AGAGCTAGAG ATTTTCACTA TTGGATCC                    3846

(2) INFORMATION FOR SEQ ID NO: 6:

(i) SEQUENCE CHARACTERISTICS:
        (A) LENGTH: 266 amino acids
        (B) TYPE: amino acid
        (D) TOPOLOGY: linear (ii) MOLECULE TYPE: protein (xi) SEQUENCE DESCRIPTION: SEQ ID NO: 6:

Gly Lys Tyr Ile Thr Phe Ile Pro Gly Pro Phe Gln Tyr Gln Leu Val
  1               5                  10                  15

Ile Lys Asn His Lys Gln Leu Ser Phe Arg Val Ser Ser Asn Lys Leu
             20                  25                  30

Ser Glu Lys Ala Phe Ser Ile Ser Gln Leu Gln Lys Asn His Asp Met
         35                  40                  45

Asn Asp Glu Leu His Leu Cys Tyr Gln Phe Leu Gln Gly Lys Ser Leu
     50                  55                  60

Asp Ile Leu Leu Glu Ser Met Met Gln Asn Leu Lys Gln Val Phe Glu
 65                  70                  75                  80

Pro Gln Leu Leu Lys Thr Thr Ser Trp Asp Thr Ala Glu Leu Tyr Pro
                 85                  90                  95

Phe Cys Ser Ser Ile Ile Phe Glu Ile Thr Phe Thr Thr Ile Tyr Gly
            100                 105                 110

Lys Val Ile Val Cys Asp Asn Asn Lys Phe Ile Ser Glu Leu Arg Asp
        115                 120                 125

Asp Phe Leu Lys Phe Asp Asp Lys Phe Ala Tyr Leu Val Ser Asn Ile
    130                 135                 140

Pro Ile Glu Leu Leu Gly Asn Val Lys Ser Ile Arg Glu Lys Ile Ile
145                 150                 155                 160

Lys Cys Phe Ser Ser Glu Lys Leu Ala Lys Met Gln Gly Trp Ser Glu
                165                 170                 175
```

```
Val Phe Gln Ser Arg Gln Asp Asp Leu Glu Lys Tyr Tyr Val His Glu
            180                 185                 190

Asp Leu Glu Ile Gly Ala His His Leu Gly Phe Leu Trp Ala Ser Val
            195                 200                 205

Ala Asn Thr Ile Pro Thr Met Phe Trp Ala Thr Tyr Tyr Leu Leu Arg
            210                 215                 220

His Pro Glu Ala Met Ala Ala Val Arg Asp Glu Ile Asp Arg Leu Leu
225                 230                 235                 240

Gln Ser Thr Gly Gln Lys Glu Gly Ser Gly Phe Pro Ile His Leu Thr
            245                 250                 255

Arg Glu Gln Leu Asp Ser Leu Ile Cys Leu
            260                 265

(2) INFORMATION FOR SEQ ID NO: 7:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 7:

CAATTCGCGG CCGCTTTTTT TTTTTTTTT                                       29

(2) INFORMATION FOR SEQ ID NO: 8:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 8:

CGACAGCAAC GG                                                         12

(2) INFORMATION FOR SEQ ID NO: 9:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 9:

AATTCCGTTG CTGTCG                                                     16

(2) INFORMATION FOR SEQ ID NO: 10:

(i) SEQUENCE CHARACTERISTICS:
            (A) LENGTH: 14 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 10:

Phe Xaa Xaa Gly Xaa Xaa Xaa Cys Xaa Gly Xaa Xaa Xaa Ala
1               5                   10
```

(2) INFORMATION FOR SEQ ID NO: 11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

GATCGCGGCC GC                                                  12

(2) INFORMATION FOR SEQ ID NO: 12:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

GGCCCTCGAG CCACCATGCA GGGGAGCCAC G                        31

(2) INFORMATION FOR SEQ ID NO: 13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 13:

GGCCGAATTC TCAGCTTCTC CAAGAA                              26

(2) INFORMATION FOR SEQ ID NO: 14:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

GACAGGTTTT GTGACCCAAA ACAAACTGGA TGGATCGCAA TC          42

(2) INFORMATION FOR SEQ ID NO: 15:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

ATCACGGAGC TCAGCACATG CAGCCTTACT CTGCAAAGCT TC          42

(2) INFORMATION FOR SEQ ID NO: 16:

(i) SEQUENCE CHARACTERISTICS:
    (A) LENGTH: 48 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 16:

AGCCTTCTGG GTCGTAGCTG ACTCCTGCTG CTGAGCTGCA ACAGCTTT                48

(2) INFORMATION FOR SEQ ID NO: 17:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

TATATCCATA CCAACTTATT GGGAGTCCCA TCCTACCTCA TCAGC                   45

(2) INFORMATION FOR SEQ ID NO: 18:

(i) SEQUENCE CHARACTERISTICS:
        (A) LENGTH: 506 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 18:

Met Met Thr Thr Ser Leu Ile Trp Gly Ile Ala Ile Ala Ala Cys Cy
1               5                  10                 15

Cys Leu Trp Leu Ile Leu Gly Ile Arg Arg Gln Thr Gly Glu Pr
            20                 25                 30

Pro Leu Glu Asn Gly Leu Gly Leu Ile Pro Tyr Leu Gly Cys Ala Le
            35                 40                 45

Gln Phe Gly Ala Asn Pro Leu Glu Phe Leu Arg Ala Asn Gln Arg Ly
        50                 55                 60

His Gly His Val Phe Thr Cys Lys Leu Met Gly Lys Tyr Val His Ph
65                 70                 75                 80

Ile Thr Asn Pro Leu Ser Tyr Lys Val Leu Cys His Gly Lys Ty
            85                 90                 95

Phe Asp Trp Lys Lys Phe His Phe Ala Thr Ser Ala Lys Ala Phe Gl
            100                105                110

His Arg Ser Ile Asp Pro Met Asp Gly Asn Thr Thr Glu Asn Ile As
        115                120                125

Asp Thr Phe Ile Lys Thr Leu Gln Gly His Ala Leu Asn Ser Leu Th
        130                135                140

Glu Ser Met Met Glu Asn Leu Gln Arg Ile Met Arg Pro Pro Val Se
145                150                155                160

Ser Asn Ser Lys Thr Ala Ala Trp Val Thr Glu Gly Met Tyr Ser Ph
            165                170                175

Cys Tyr Arg Val Met Phe Glu Ala Gly Tyr Leu Thr Ile Phe Gly Ar
            180                185                190

Asp Leu Thr Arg Arg Asp Thr Gln Lys Ala His Ile Leu Asn Asn Le
        195                200                205

-continued

```
Asp Asn Phe Lys Gln Phe Asp Lys Val Phe Pro Ala Leu Val Ala Gl
    210                 215                 220
Leu Pro Ile His Met Phe Arg Thr Ala His Asn Ala Arg Glu Lys Le
225                 230                 235                 240
Ala Glu Ser Leu Arg His Glu Asn Leu Gln Lys Arg Glu Ser Ile Se
                245                 250                 255
Glu Leu Ile Ser Leu Arg Met Phe Leu Asn Asp Thr Leu Ser Thr Ph
                260                 265                 270
Asp Asp Leu Glu Lys Ala Lys Thr His Leu Val Val Leu Trp Ala Se
            275                 280                 285
Gln Ala Asn Thr Ile Pro Ala Thr Phe Trp Ser Leu Phe Gln Met Il
        290                 295                 300
Arg Asn Pro Glu Ala Met Lys Ala Ala Thr Glu Val Lys Arg Th
305                 310                 315                 320
Leu Glu Asn Ala Gly Gln Lys Val Ser Leu Glu Gly Asn Pro Ile Cy
                325                 330                 335
Leu Ser Gln Ala Glu Leu Asn Asp Leu Pro Val Leu Asn Ser Ile Il
                340                 345                 350
Lys Glu Ser Leu Arg Leu Ser Ser Ala Ser Leu Asn Ile Arg Thr Al
            355                 360                 365
Lys Glu Asp Phe Thr Leu His Leu Glu Asp Gly Ser Tyr Asn Ile Ar
370                 375                 380
Lys Asp Ser Ile Ile Ala Leu Tyr Pro Gln Leu Met His Leu Asp Pr
385                 390                 395                 400
Glu Ile Tyr Pro Asp Pro Leu Thr Phe Lys Tyr Asp Arg Tyr Leu As
                405                 410                 415
Glu Asn Gly Lys Thr Lys Thr Thr Phe Tyr Cys Asn Gly Leu Lys Le
                420                 425                 430
Lys Tyr Tyr Tyr Met Pro Phe Gly Ser Gly Ala Thr Ile Cys Pro Gl
            435                 440                 445
Arg Leu Phe Ala Ile His Glu Ile Lys Gln Phe Leu Ile Leu Met Le
450                 455                 460
Ser Tyr Phe Glu Leu Glu Leu Ile Glu Gly Gln Ala Lys Cys Pro Pr
465                 470                 475                 480
Leu Asp Gln Ser Arg Ala Gly Leu Gly Ile Leu Pro Pro Leu Asn As
                485                 490                 495
Ile Glu Phe Lys Tyr Lys Phe Lys His Leu
                500                 505
```

(2) INFORMATION FOR SEQ ID NO: 19:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 19:

```
Phe Gly Leu Gly Thr Ser Lys Cys Pro Gly Arg Tyr Phe Ala
1               5                   10
```

(2) INFORMATION FOR SEQ ID NO: 20:

(i) SEQUENCE CHARACTERISTICS:
        (A) LENGTH: 14 amino acids
        (B) TYPE: amino acid (C) STRANDEDNESS: <Unknown>
            (D) TOPOLOGY: linear (ii) MOLECULE TYPE: peptide (xi) SEQUENCE DESCRIPTION: SEQ ID NO: 20:

Phe Gly Ser Gly Ala Thr Ile Cys Pro Gly Arg Leu Phe Ala
1               5                   10

(2) INFORMATION FOR SEQ ID NO: 21:

(i) SEQUENCE CHARACTERISTICS:
            (A) LENGTH: 14 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 21:

Phe Gly Ala Gly Pro Arg Ser Cys Val Gly Glu Met Leu Ala
1               5                   10

(2) INFORMATION FOR SEQ ID NO: 22:

(i) SEQUENCE CHARACTERISTICS:
            (A) LENGTH: 14 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 22:

Phe Gly Phe Gly Met Arg Gln Cys Leu Gly Arg Arg Leu Ala
1               5                   10

(2) INFORMATION FOR SEQ ID NO: 23:

(i) SEQUENCE CHARACTERISTICS:
            (A) LENGTH: 14 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 23:

Phe Gly Cys Gly Ala Arg Val Cys Leu Gly Glu Pro Val Ala
1               5                   10

(2) INFORMATION FOR SEQ ID NO: 24:

(i) SEQUENCE CHARACTERISTICS:
            (A) LENGTH: 14 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 24:

Phe Gly Trp Gly Val Arg Gln Cys Leu Gly Arg Arg Ile Ala
1               5                   10

(2) INFORMATION FOR SEQ ID NO: 25:

(i) SEQUENCE CHARACTERISTICS:
            (A) LENGTH: 14 amino acids

```
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 25:

Phe Gly Tyr Gly Val Arg Ala Cys Leu Gly Arg Arg Ile Ala
1               5                   10

(2) INFORMATION FOR SEQ ID NO: 26:

(i) SEQUENCE CHARACTERISTICS:
            (A) LENGTH: 15 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 26:

Val Cys Leu Glu Ser Thr Ile Leu Glu Val Leu Arg Leu Cys Ser
1               5                   10                  15

(2) INFORMATION FOR SEQ ID NO: 27:

(i) SEQUENCE CHARACTERISTICS:
            (A) LENGTH: 15 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 27:

Pro Val Leu Asn Ser Ile Ile Lys Glu Ser Leu Arg Leu Ser Ser
1               5                   10                  15

(2) INFORMATION FOR SEQ ID NO: 28:

(i) SEQUENCE CHARACTERISTICS:
            (A) LENGTH: 15 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 28:

Val Leu Leu Glu His Thr Ile Arg Glu Val Leu Arg Ile Arg Pro
1               5                   10                  15

(2) INFORMATION FOR SEQ ID NO: 29:

(i) SEQUENCE CHARACTERISTICS:
            (A) LENGTH: 15 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 29:

Pro Leu Leu Arg Ala Ala Leu Lys Glu Thr Leu Arg Leu Tyr Pro
1               5                   10                  15

(2) INFORMATION FOR SEQ ID NO: 30:

(i) SEQUENCE CHARACTERISTICS:
```

(A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 30:

Pro Leu Leu Asn Ala Thr Ile Ala Glu Val Leu Arg Leu Pro Val
1                 5                  10                  15

(2) INFORMATION FOR SEQ ID NO: 31:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 31:

Pro Leu Leu Lys Ala Ser Ile Lys Glu Thr Leu Arg Leu His Pro
1                 5                  10                  15

(2) INFORMATION FOR SEQ ID NO: 32:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 32:

Pro Leu Leu Lys Ala Val Leu Lys Glu Thr Leu Arg Leu Tyr Pro
1                 5                  10                  15

(2) INFORMATION FOR SEQ ID NO: 33:

(i) SEQUENCE CHARACTERISTICS:
        (A) LENGTH: 266 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 33:

Gly Lys Tyr Ile Thr Phe Val Leu Asn Pro Phe Gln Tyr Gln Tyr Va
1                 5                  10                  15

Thr Lys Asn Pro Lys Gln Leu Ser Phe Gln Lys Phe Ser Ser Arg Le
                20                  25                  30

Ser Ala Lys Ala Phe Ser Val Lys Leu Leu Thr Asp Asp Le
            35                  40                  45

Asn Glu Asp Val His Arg Ala Tyr Leu Leu Gln Gly Lys Pro Le
            50                  55                  60

Asp Ala Leu Leu Glu Thr Met Ile Gln Glu Val Lys Glu Leu Phe Gl
65                  70                  75                  80

Ser Gln Leu Leu Lys Ile Thr Asp Trp Asn Thr Glu Arg Ile Phe Al
                85                  90                  95

Phe Cys Gly Ser Leu Val Phe Glu Ile Thr Phe Ala Thr Leu Tyr Gl
                100                 105                 110

Lys Ile Leu Ala Gly Asn Lys Lys Gln Ile Ile Ser Glu Leu Arg As

```
              115                 120                 125
Asp Phe Phe Lys Phe Asp Asp Met Phe Pro Tyr Leu Val Ser Asp Il
    130                 135                 140
Pro Ile Gln Leu Leu Arg Asn Glu Glu Ser Met Gln Lys Lys Ile Il
145                 150                 155                 160
Lys Cys Leu Thr Ser Glu Lys Val Ala Gln Met Gln Gly Gln Ser Ly
                165                 170                 175
Ile Val Gln Glu Ser Gln Asp Leu Leu Lys Arg Tyr Tyr Arg His As
            180                 185                 190
Asp Ser Glu Ile Gly Ala His His Leu Gly Phe Leu Trp Ala Ser Le
        195                 200                 205
Ala Asn Thr Ile Pro Ala Met Phe Trp Ala Met Tyr Tyr Ile Leu Ar
    210                 215                 220
His Pro Glu Ala Met Glu Ala Leu Arg Asp Glu Ile Asp Ser Phe Le
225                 230                 235                 240
Gln Ser Thr Gly Gln Lys Lys Gly Pro Gly Ile Ser Val His Phe Th
                245                 250                 255
Arg Glu Gln Leu Asp Ser Leu Val Cys Leu
            260                 265
```

(2) INFORMATION FOR SEQ ID NO: 34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 34:

CTCCAGCCAT GGTCCTCG                                                      18

(2) INFORMATION FOR SEQ ID NO: 35:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 35:

GTCTCGCCAT GCTGCTCC                                                      18

(2) INFORMATION FOR SEQ ID NO: 36:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 36:

CAGCCACCAT GTGGGAGC                                                     18

(2) INFORMATION FOR SEQ ID NO: 37:

(i) SEQUENCE CHARACTERISTICS:
        (A) LENGTH: 18 base pairs (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 37:

TCGTCGGGAT GCAGGGAG                                                     18

(2) INFORMATION FOR SEQ ID NO: 38:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 38:

TTTGCAAAAT GATGACCA                                                     18

(2) INFORMATION FOR SEQ ID NO: 39:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 39:

TTTGCAAAAT GATGACTA                                                     18

(2) INFORMATION FOR SEQ ID NO: 40:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 40:

TTTGCAAAAT GATGAGCA                                                     18

(2) INFORMATION FOR SEQ ID NO: 41:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 41:

TCGGATCCAT GGCTGCGC                                                     18

(2) INFORMATION FOR SEQ ID NO: 42:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 42:

CACGATCTAT GGCTGTGT                                                            18

(2) INFORMATION FOR SEQ ID NO: 43:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 43:

TCGCCACCAT GCAGGGAG                                                            18

(2) INFORMATION FOR SEQ ID NO: 44:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 44:

GGCCCTCGAG CCACCATGCA GGGAGCCACG                                               30

(2) INFORMATION FOR SEQ ID NO: 45:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 45:

GGCCGAATTC TCAGCTTCTC CAAGA                                                    25